United States Patent
Zuo et al.

(10) Patent No.: US 12,427,149 B2
(45) Date of Patent: Sep. 30, 2025

(54) METHODS AND COMPOSITIONS FOR THE PREVENTION AND TREATMENT OF HEARING LOSS

(71) Applicant: Ting Therapeutics, Inc., San Diego, CA (US)

(72) Inventors: Jian Zuo, Carlsbad, CA (US); Tal Teitz, Carlsbad, CA (US)

(73) Assignee: Ting Theropeutics, Inc., San Diego, CA (US)

( * ) Notice: Subject to any disclaimer, the term of this patent is extended or adjusted under 35 U.S.C. 154(b) by 251 days.

(21) Appl. No.: 17/736,330

(22) Filed: May 4, 2022

(65) Prior Publication Data

US 2022/0265660 A1    Aug. 25, 2022

Related U.S. Application Data

(60) Division of application No. 17/580,755, filed on Jan. 21, 2022, now Pat. No. 11,433,073, which is a continuation of application No. PCT/US2020/063595, filed on Dec. 7, 2020.

(60) Provisional application No. 62/947,059, filed on Dec. 12, 2019.

(51) Int. Cl.
*A61P 27/16*      (2006.01)
*A61K 31/437*     (2006.01)
*A61K 31/4439*    (2006.01)
*A61K 31/4709*    (2006.01)
*A61K 31/506*     (2006.01)
*A61K 31/519*     (2006.01)

(52) U.S. Cl.
CPC .......... *A61K 31/519* (2013.01); *A61K 31/437* (2013.01); *A61K 31/4439* (2013.01); *A61K 31/4709* (2013.01); *A61K 31/506* (2013.01); *A61P 27/16* (2018.01)

(58) Field of Classification Search
CPC .... A61P 27/16; A61K 31/506; A61K 2300/00
See application file for complete search history.

(56) References Cited

U.S. PATENT DOCUMENTS

| | | | |
|---|---|---|---|
| 7,465,728 B2 | 12/2008 | Newcombe et al. | |
| 8,703,781 B2 | 4/2014 | Dumble et al. | |
| 8,937,095 B2 | 1/2015 | Zahn et al. | |
| 9,258,235 B2 | 2/2016 | Báder et al. | |
| 9,358,235 B2 | 6/2016 | Bollag et al. | |
| 9,572,815 B2 | 2/2017 | Zuo et al. | |
| 9,814,714 B2 | 11/2017 | Ibrahim et al. | |
| 9,884,868 B2 | 2/2018 | Kinsella et al. | |
| 9,938,273 B2 | 4/2018 | Wu et al. | |
| 10,004,803 B2 | 6/2018 | Mannick et al. | |
| 10,065,934 B2 | 9/2018 | Cheng et al. | |
| 10,160,755 B2 | 12/2018 | Lin et al. | |
| 10,286,069 B2 | 5/2019 | Mannick et al. | |
| 10,428,067 B2 | 10/2019 | Zhang et al. | |
| 10,449,193 B2 | 10/2019 | Helson et al. | |
| 10,485,791 B2 | 11/2019 | Wrobel et al. | |
| 10,639,298 B2 | 5/2020 | Wrobel et al. | |
| 10,669,296 B2 | 6/2020 | Martinez et al. | |
| 10,822,337 B2 | 11/2020 | Gelman et al. | |
| 10,973,809 B2 | 4/2021 | Miao et al. | |
| 11,024,468 B2 | 6/2021 | Luo et al. | |
| 11,090,307 B2 | 8/2021 | Wang et al. | |
| 11,141,483 B2 | 10/2021 | Makings et al. | |
| 11,433,073 B2 * | 9/2022 | Zuo ................... A61K 31/4709 |
| 2009/0142337 A1 | 6/2009 | Squires | |
| 2010/0021420 A1 | 1/2010 | Lyons et al. | |
| 2013/0085112 A1 | 4/2013 | Collard et al. | |
| 2014/0018372 A1 | 1/2014 | Maier et al. | |
| 2014/0275183 A1 | 9/2014 | Yamamoto et al. | |
| 2015/0140036 A1 | 5/2015 | Mannick et al. | |
| 2015/0252428 A1 | 9/2015 | Comper et al. | |
| 2015/0352086 A1 | 12/2015 | Koomen et al. | |
| 2016/0089371 A1 | 3/2016 | Liu et al. | |
| 2017/0143682 A1 | 5/2017 | Melin | |
| 2017/0327557 A1 | 11/2017 | Chen | |
| 2018/0015137 A1 | 1/2018 | Keizer | |
| 2018/0161340 A1 | 6/2018 | Zuo et al. | |
| 2018/0333411 A1 | 11/2018 | Srinivasan et al. | |
| 2018/0338979 A1 * | 11/2018 | Laquerre ................. A61P 35/00 |
| 2019/0083521 A1 | 3/2019 | Klaus et al. | |
| 2019/0209532 A1 | 7/2019 | Pelletier et al. | |
| 2019/0233895 A1 | 8/2019 | Kurzrock et al. | |
| 2019/0365897 A1 | 12/2019 | Garcia-Guzman et al. | |
| 2019/0367903 A1 | 12/2019 | Domenyuk et al. | |
| 2020/0030355 A1 | 1/2020 | Klaus et al. | |
| 2020/0170872 A1 | 6/2020 | Lee et al. | |
| 2021/0220300 A1 | 7/2021 | Cohen | |

FOREIGN PATENT DOCUMENTS

| | | |
|---|---|---|
| CA | 2974623 A1 | 7/2016 |
| CN | 104211692 A | 12/2014 |
| CN | 104447701 B | 3/2019 |
| CN | 109475541 A | 3/2019 |
| GB | 201802307 | 3/2018 |
| WO | 2015104292 A3 | 2/2016 |
| WO | 2016118014 A2 | 7/2016 |
| WO | 2016205806 A1 | 12/2016 |
| WO | 2017162510 A1 | 9/2017 |
| WO | 2018204226 A1 | 11/2018 |
| WO | 2019103984 A1 | 5/2019 |

(Continued)

OTHER PUBLICATIONS

Byth et al., "AZD5438, a potent oral inhibitor of cyclin-dependent kinases 1, 2, and 9, leads to pharmacodynamic changes and potent antitumor effects in human tumor xenografts," Mol. Cancer Ther. Jul. 2009;8(7):1856-66. PMID: 19509270. (Year: 2009).*

(Continued)

*Primary Examiner* — Theodore R. Howell
(74) *Attorney, Agent, or Firm* — Susan Fentress; Verritay Croup IP, PLLC

(57) ABSTRACT

Method, kit and pharmaceutical compositions using an inhibitor of EGFR signaling for prevention or treatment of hearing loss are described.

9 Claims, 11 Drawing Sheets

Specification includes a Sequence Listing.

(56) References Cited

FOREIGN PATENT DOCUMENTS

| WO | 2020084105 A3 | 8/2020 |
| WO | 2022020114 A2 | 1/2022 |
| WO | 2022020114 A3 | 3/2022 |

OTHER PUBLICATIONS

Tsai et al., "Discovery of a selective inhibitor of oncogenic B-Raf kinase with potent antimelanoma activity," Proc. Natl. Acad. Sci. U.S.A. Feb. 26, 2008;105(8):3041-46. PMID: 18287029. (Year: 2008).*
Teitz et al., "CDK2 inhibitors as candidate therapeutics for cisplatin- and noise-induced hearing loss," J. Exp. Med. 2018;215(4): 1187-203. PMID: 29514916. (Year: 2018).*
Brighton, Hailey E., et al. "New mechanisms of resistance to MEK inhibitors in melanoma revealed by intravital imaging." Cancer Research 78.2 (2018): 542-557.
Supplemental European Search Report in EP Application No. 20900420.9, dated Apr. 10, 2024, in 4 pages.
Search Report in CN Application No. 202080086445.X, dated Dec. 5, 2023, in 3 pages.
Amaravadi RK, Hamilton KE, Ma X, Piao S, Portillo AD, Nathanson KL, Carlino MS, Long GV, Puzanov I, Xu X, Morrissette JJ, Tsai KY, Flaherty KT, Sosman JA, Goodman GR, McArthur GA, Rustgi AK, Metz DC, Schuchter LM, Chapman PB, Sepulveda AR. Multiple Gastrointestinal Polyps in Patients Treated with BRAF Inhibitors. Clin Cancer Res. Dec. 1, 2015;21(23):5215-21. doi: 10.1158/1078-0432.CCR-15-0469. Epub Jul. 22, 2015. PMID: 26202952; PMCID: PMC4668213.
Ascierto, P.A., Simeone, E., Sileni, V.C. et al. Sequential treatment with ipilimumab and BRAF inhibitors in patients with metastatic melanoma: data from the Italian ipilimumab expanded access programme (EAP). j. immunotherapy cancer 1, P69 (2013). https://doi.org/10.1186/2051-1426-1-S1-P69.
Atikinson et al. "Hair Cell Regeneration after ATOH1 Gene Therapy in the Cochlea of Profoundly Deaf Adault Guinea Pigs," PLoS ONE, Jul. 18, 2014 (Jul. 18, 2014), vol. 9, Iss. 7, pp. 1-11. entire document.
Boanza et al. "A primary role for the epidermal growth factor receptor in ommatidial spacing in the Drosophilia eye," Current Biology, Mar. 20, 2001 (Mar. 20, 2001), vol. 9, Iss. 6, pp. 396-404. entire document.
Gautschi O, Milia J, Cabarrou B, Bluthgen MV, Besse B, Smit EF, Wolf J, Peters S, Früh M, Koeberle D, Oulkhouir Y, Schuler M, Curioni-Fontecedro A, Huret B, Kerjouan M, Michels S, Pall G, Rothschild S, Schmid-Bindert G, Scheffler M, Veillon R, Wannesson L, Diebold J, Zalcman G, Filleron T, Mazières J. Targeted Therapy for Patients with BRAF-Mutant Lung Cancer: Results from the European EURAF Cohort. J Thorac Oncol. Oct. 2015;10(10):1451-7. doi: 10.1097/JTO.0000000000000625. PMID: 26200454.
Groseclose MR, Laffan SB, Frazier KS, Hughes-Earle A, Castellino S. Imaging MS in Toxicology: an Investigation of Juvenile Rat Nephrotoxicity Associated with Dabrafenib Administration. J Am Soc Mass Spectrom. Jun. 2015;26 (6):887-98. doi: 10.1007/s13361-015-1103-4. Epub Mar. 25, 2015. PMID: 25804893; PMCID: PMC4422858.
Harttrampf AC, Lacroix L, Deloger M, Deschamps F, Puget S, Auger N, Vielh P, Varlet P, Balogh Z, Abbou S, Allorant A, Valteau-Couanet D, Sarnacki S, Gamiche-Rolland L, Meurice G, Minard-Colin V, Grill J, Brugieres L, Dufour C, Gaspar N, Michiels S, Vassal G, Soria JC, Geoerger B. Molecular Screening for Cancer Treatment Optimization (MOSCATO-01) in Pediatric Patients: a Single-Institutional Prospective Molecular Stratification Trial. Clin Cancer Res. Oct. 15, 2017;23(20):6101-6112. doi: 10.1158/1078-0432.CCR-17-0381. Epub Jul. 21, 2017. PMID: 28733441.
Hazlitt et al., "Development of Second-Generation CDK2 Inhibitors for the prevention of Cisplatin-Induced Hearing Loss," J. Med Chem. Sep. 13, 2018:61(17):7700-7709.
Hecht M, Meier F, Zimmer L, Polat B, Loquai C, Weishaupt C, Forschner A, Gutzmer R, Utikal JS, Goldinger SM, Geier M, Hassel JC, Balermpas P, Kiecker F, Rauschenberg R, Dietrich U, Clemens P, Berking C, Grabenbauer G, Schadendorf D, Grabbe S, Schuler G, Fietkau R, Distel LV, Heinzerling L. Clinical outcome of concomitant vs interrupted BRAF inhibitor therapy during radiotherapy in melanoma patients. Br J Cancer. Mar. 20, 2018;118 (6):785-792. doi: 10.1038/bjc.2017.489. Epub Feb. 13, 2018. PMID: 29438368; PMCID: PMC5886123.
Jarman et al. "The role of Atonal transcription factors in the development of machanosensitive cells," Seminars in Cell and Developmental Biology, May 1, 2013 (May 1, 2013, Vool. 24 Iss. 5, pp. 438-447. Entire document.
Johnson DB, Flaherty KT, Weber JS, Infante JR, Kim KB, Kefford RF, Hamid O, Schuchter L, Cebon J, Sharfman WH,McWilliams RR, Sznol M, Lawrence DP, Gibney GT, Burris HA 3rd, Falchook GS, Algazi A, Lewis K, Long GV, Patel K, Ibrahim N, Sun P, Little S, Cunningham E, Sosman JA, Daud A, Gonzalez R. Combined BRAF (Dabrafenib) and MEK inhibition (Trametinib) in patients with BRAFV600-mutant melanoma experiencing progression with single-agent BRAF inhibitor. J Clin Oncol. Nov. 20, 2014;32(33):3697-704. doi: 10.1200/JCO.2014.57.3535. Epub Oct. 6, 2014.
Lampson BL, Nishino M, Dahlberg SE, Paul D, Santos AA, Jänne PA, Oxnard GR. Activity of erlotinib when dosed below the maximum tolerated dose for EGFR-mutant lung cancer: Implications for targeted therapy development. Cancer. Nov. 15, 2016;122(22):3456-3463. doi: 10.1002/cncr.30270. Epub Aug. 15, 2016. PMID: 27525836; PMCID: PMC5311035.
Lee Young, International Search Report Written opinion concerning patentability PCT/US20/63595, International Searching Authority, Jun. 28, 2021, 1-5.
Liniker E, Menzies AM, Kong BY, Cooper A, Ramanujam S, Lo S, Kefford RF, Fogarty GB, Guminski A, Wang TW, Carlino MS, Hong A, Long GV. Activity and safety of radiotherapy with anti-PD-1 drug therapy in patients with metastatic melanoma. Oncoimmunology. Aug. 19, 2016;5(9):e1214788. doi: 10.1080/2162402X.2016.1214788. PMID: 27757312; PMCID: PMC5048757.
Menzies AM, Wilmott JS, Drummond M, Lo S, Lyle M, Chan MM, Thompson JF, Guminski A, Carlino MS, Scolyer RA, Kefford RF, Long GV. Clinicopathologic features associated with efficacy and long-term survival in metastatic melanoma patients treated with BRAF or combined BRAF and MEK inhibitors. Cancer. Nov. 1, 2015;121(21):3826-35. doi: 10.1002/cncr.29586. Epub Jul. 28, 2015. PMID: 26218930.
Prescribing information for TAFLINLAR (dabrafenib), revised Oct. 2019, retrieved from fda.gov on Apr. 12, 2022. (Year: 2019).
Theodore Howell, International Preliminary Report onPatentability PCT/US20/63595, International Preliminary Examination Authority, Nov. 3, 2021, 1-6.
Villaruz LC, Socinski MA, Abberbock S, Berry LD, Johnson BE, Kwiatkowski DJ, Iafrate AJ, Varella-Garcia M, Franklin WA, Camidge DR, Sequist LV, Haura EB, Ladanyi M, Kurland BF, Kugler K, Minna JD, Bunn PA, Kris MG. Clinicopathologic features and outcomes of patients with lung adenocarcinomas harboring BRAF mutations in the Lung Cancer Mutation Consortium. Cancer. Feb. 1, 2015;121(3):448-56. doi: 10.1002/cncr.29042. Epub Oct. 1, 2014. PMID: 25273224; PMCID: PMC4305000.
DI Veroli et al. Combenefit: an Interactive Platform for the Analysis and Visualization of Drug Combinations Bioinfor. Adv. Access (Apr. 25, 2016).
Salehi P, Zallocchi M, Vijayakumar S, Urbanek M, Giffen KP, Li Y, Hati S, Zuo J. In silico transcriptomics identifies FDA-approved drugs and biological pathways for protection against cisplatin-induced hearing loss. Revision. BioRxiv preprint for eLife (Jan. 28, 2022).
Vijayakumar S, DiGuiseppi JA, Dabestani J, Ryan WG, Vielman Quevedo R, Li Y, Diers J, Tu S, Fleegel J, Nguyen C, Rhoda LM, Sajid Imami A, Ali Hamoud A, Lovas S, McCullumsmith R, Zallocchi M, Zuo J. In Silico Transcriptome-based Screens Identify Epidermal Growth Factor Receptor Inhibitors as Therapeutics for Noise-induced Hearing Loss. Science Advances 10, eadk2299 (2024).

\* cited by examiner

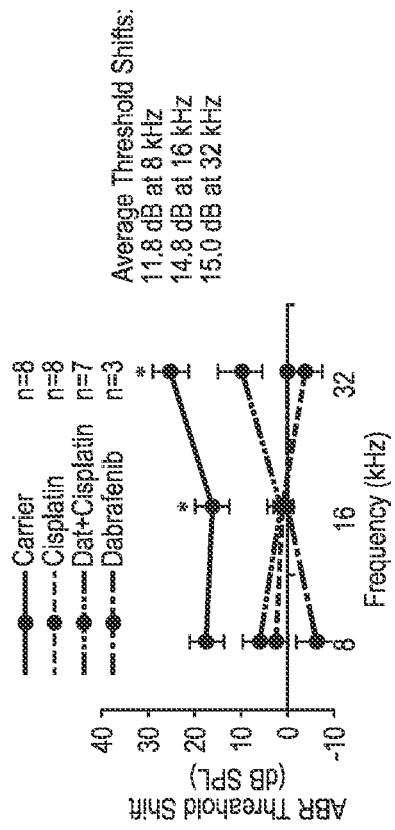
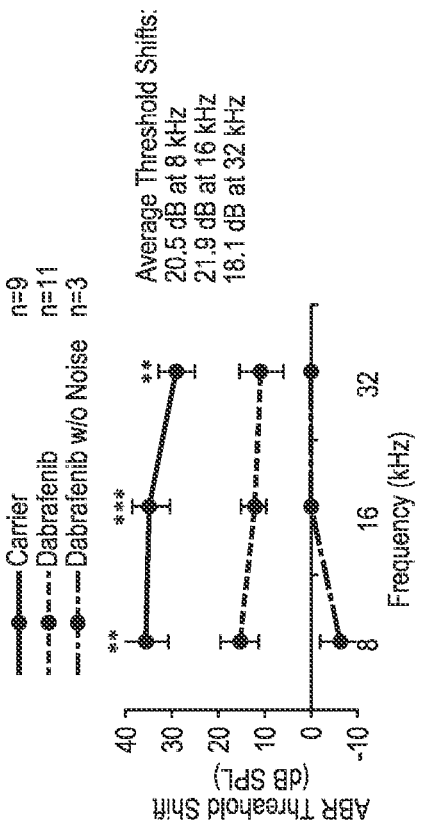
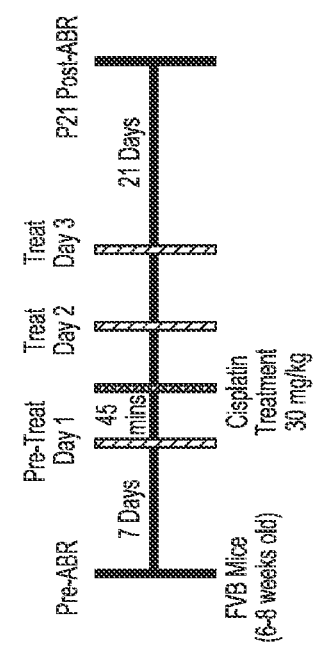
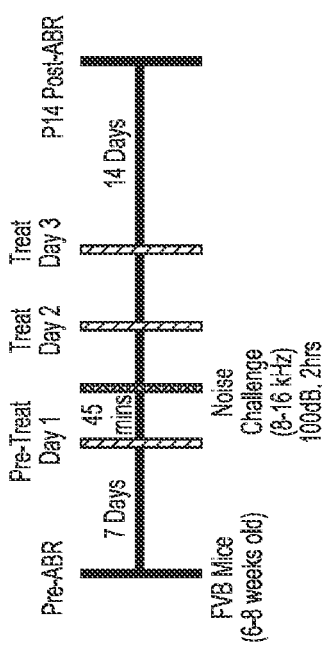

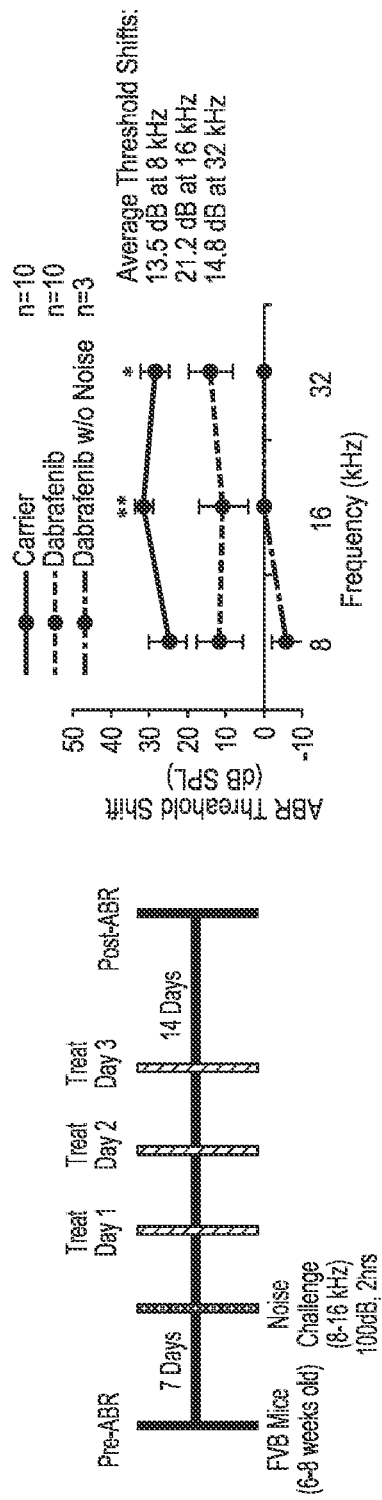
FIG. 8B
FIG. 8A
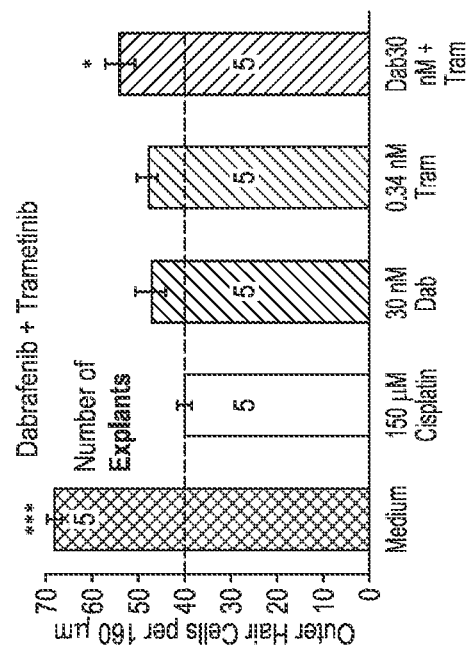
FIG. 9

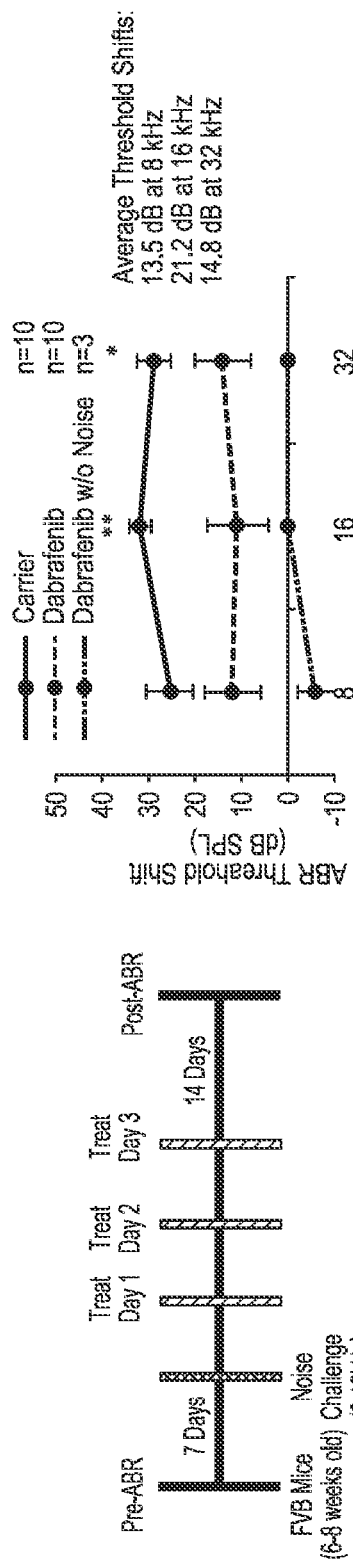
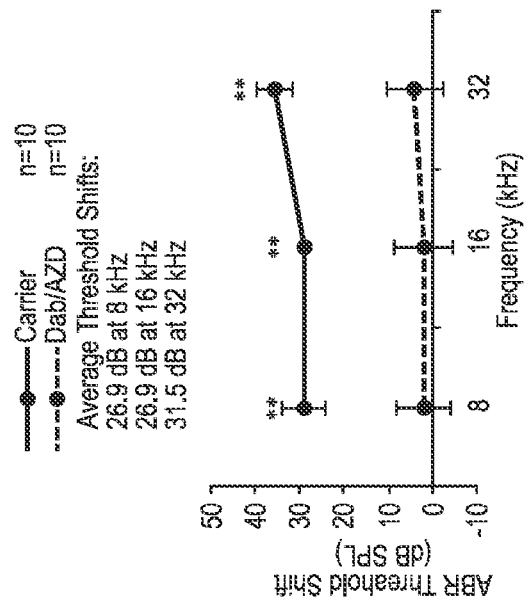
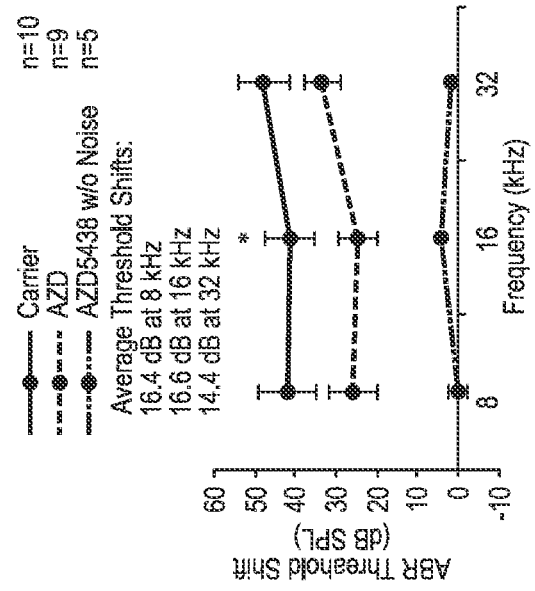

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Ala Ala Asn Ala Arg Glu Arg Arg Met His Gly Leu Asn His Ala
1               5                   10                  15

Phe Asp Gln Leu Arg
            20

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide

<400> SEQUENCE: 2

Leu Leu Leu Trp Ala Leu Gly Ile Gly Leu Phe Met Arg Arg Arg His
1               5                   10                  15

Ile Val Arg Lys Arg Thr Leu Arg Arg Leu Leu Gln Glu Arg Glu Leu
            20                  25                  30

Val Glu Pro Leu Thr Pro Ser
        35
```

METHODS AND COMPOSITIONS FOR THE PREVENTION AND TREATMENT OF HEARING LOSS

CROSS REFERENCE TO RELATED APPLICATIONS

This application is a divisional patent application of U.S. Pat. No. 17,580,755 filed Jan. 21, 2022, which is a continuation filed under 35 U.S.C. section 365(c) of PCT/US2020/63595 application filed on Dec. 7, 2020 and U.S. provisional patent application Ser. No. 62/947,059 filed on Dec. 12, 2019, under 35 U.S.C. § 111 (a) (hereby specifically incorporated herein by reference).

REFERENCE TO SEQUENCE LISTING, A TABLE FOR A COMPUTER PROGRAM LISTING, COMPACT DISC APPENDIX

Incorporation by reference of the material in the ASCII text file: Applicant hereby specifically incorporates by reference the file PATENTIN_ST25, created on Apr. 22, 2022 and 4kb in size.

INTRODUCTION

This invention was made with government support under Grant Numbers DC006471 DC015010, DC015444, DC013879, DC013232, and CA021765 awarded by the National Institutes of Health and Grant Numbers N00014-09-V-1014, N00014-12-V-0191, N00014-12-V-0775, and N00014-16-V-2315 awarded by the Office of Naval Research. The government has certain rights in the invention.

BACKGROUND

The ear is a complex organ composed of a labyrinth of structures responsible for hearing and balance. Perception of both hearing and balance lies in the ability of inner ear structures to transform mechanical stimuli to impulses recognized by the brain. The sensory receptors responsible for hearing are located in the cochlea, a spiral-shaped canal filled with fluid. Within the cochlea is the organ of Corti, which is lined with columnar sensory hair cells bridging the basilar membrane and the tectorial membrane. As sound waves pass through the organ of Corti, the basilar membrane vibrates causing the hair cells to bend back and forth. The movement depolarizes the hair cell, leading to release of neurotransmitters to the auditory nerve, which carries the impulse to the brain.

The inner-ear cochlear sensory epithelium is post-mitotic after birth and, in mice, exhibits only limited spontaneous regeneration during the first week after birth. In adult mammals, hair cells cannot regenerate spontaneously and damage to sensory hair cells therefore leads to permanent hearing loss in mammals.

Inner ear sensory hair cells are prone to damages caused by noise, antibiotics, cisplatin during chemotherapy, or aging. Currently there are no FDA-approved otoprotective agents for preventions and treatments of hearing loss.

SUMMARY OF THE INVENTION

The invention provides a method for the treatment or prevention of hearing loss by administering to an animal in need thereof an inhibitor of epidermal growth factor receptor (EGFR) signaling. In other embodiments, the method further includes administering one or more otoprotective agents. In particular the inventive subject matter includes: Use of an inhibitor of epidermal growth factor receptor (EGFR) signaling, for the treatment or prevention of hearing loss, wherein the inhibitor of EGFR signaling inhibits the expression or activity of at least one of PAN-AUR, ErBb-2, MEK, or a cell cycle-associated protein kinase consisting of: Her-2, Aurora Kinase, B-Raf or PDGFR.

In further embodiments, the inhibitor of EGFR signaling inhibits the expression or activity of EGFR, Ras, Raf, MEK, ERK/MAPK, JAK, STAT, PI3K, AKT, mTOR, NCK, PAK, JNK, PLC, PKC, or a cell cycle-associated protein kinase inhibitor (e.g., Her-2, Aurora Kinase, B-Raf or PDGFR). In other embodiments, the inhibitor is an inhibitory RNA, antibody or small organic molecule.

An further embodiments, a pharmaceutical composition made of a synergistic combination of at least two inhibitors of epidermal growth factor receptor (EGFR) signaling, wherein the inhibitor of EGFR signaling inhibits the expression or activity of EGFR, Ras, Raf, MEK, ERK/MAPK, JAK, STAT, PI3K, AKT, NCK, PAK, JNK, PLC, PKC or a cell cycle-associated protein kinase inhibitor is provided.

Another aspect of the inventive subject matter includes a kit made of a first isolated inhibitor of EGFR signaling; wherein the first inhibitor of EGFR signaling inhibits the expression or activity of EGFR, Ras, Raf, MEK, ERK/MAPK, JAK, STAT, PI3K, AKT, NCK, PAK, JNK, PLC, PKC or a cell cycle-associated protein kinase inhibitor and a second isolated inhibitor of EGFR signaling; wherein the inhibitor of EGFR signaling inhibits the expression activity of EGFR, Ras, Raf, MEK, ERK/MAPK, JAK, STAT, PI3K, AKT, NCK, PAK, JNK, PLC, PKC or a cell cycle-associated protein kinase inhibitor, wherein the first inhibitor is different than the second inhibitor.

BRIEF DESCRIPTION OF THE DRAWINGS

FIG. 6A shows schedule of administration of dabrafenib (100 mg/kg) and cisplatin (30 mg/kg) to adult FVB mice (males and females).

FIG. 6B shows reduced ABR threshold shifts of 11.8-15.0 dB in average were recorded on day 21 after first day of cisplatin (30 mg/kg) and dabrafenib (100 mg/kg) co-treatment, mean±SEM, *, P<0.05, compared to cisplatin alone by two-way ANOVA followed by a Bonferroni comparison.

FIG. 7A shows schedule of administration of dabrafenib (100 mg/kg) and noise exposure to adult FVB mice (males and females).

FIG. 7B shows reduced ABR threshold shifts of 18.1-21.9 dB in average were recorded on day 14 after first day of dabrafenib (100 mg/kg) and noise exposure, mean±SEM, , P<0.01, *, P<0.001, compared to carrier by two-way ANOVA followed by a Bonferroni comparison.

FIG. 8A shows schedule of administration of dabrafenib (60 mg/kg x2 daily) and noise exposure to adult FVB mice (males and females).

FIG. 8B shows reduced ABR threshold shifts of 13.5-21.2 dB on average were recorded on day 14 after first day of dabrafenib (60 mg/kg x2 daily) and noise exposure, mean±SEM, , P<0.01, *, P<0.001, compared to carrier by two-way ANOVA followed by a Bonferroni comparison.

FIGS. 13A-13D show protection against noise injury in mice by oral delivery of a combination of inhibitors (Dabrafenib 60 mg/kg x2 daily, AZD543B 35 mg/kg X2 daily).

DETAILED DESCRIPTION OF THE INVENTION

It has now been found that inhibitors of EGFR and proteins downstream or associated therewith protect hair cells damaged by cisplatin, antibiotics, noise, aging or other ototoxic insults. Accordingly, this inventive provides compositions and methods for the prevention and treatment of hearing loss using an inhibitor of EGFR. Ideally, the inventive methods prophylactically or therapeutically treat an animal, preferably a mammal (e.g., a human), for at least one disorder associated with loss or damage of sensory hair cells, e.g., disorders of the ear associated with damage of sensory hair cells (such as hearing loss or balance disorders). The inventive methods also are useful in maintaining a level of sensory perception, i.e., controlling the loss of perception of environmental stimuli caused by, for instance, the aging process or ototoxic agents. Inhibitors of EGFR and proteins downstream or associated therewith provide a therapeutic effect as summarized in Table 1.

TABLE 1

| Compound | Target kinase | Clinical status | Number of additional hits for target kinase | HEI-OC1 cell line $IC_{50}$ (μM) | Zebrafish protection (μM) | Mouse cochlear explant $IC_{50}$ (μM) | Therapeutic index in mouse cochlear explant ($LD_{50}/IC_{50}$) |
|---|---|---|---|---|---|---|---|
| Mubritinib | ErBb-2 (Her-2) | Phase 1 | 5 | 0.039 | 0.001-0.100 | 0.002 | >500 |
| Dabrafenib | B-Raf | FDA Approved | 4 | 13.47 | 0.100 | 0.030 | >2,000 |
| Crenolanib | PDGFR | Phases 1, 3 | 5 | 2.40 | 0.001-1.000 | 0.350 | >14 |
| SNS-314 | Aurora Kinases A, B, C | Phase 1 | 2 | 7.49 | 0.001-0.050 | 0.050 | >100 |

FIG. 9 shows Testing a B-Raf/MEK1/2 inhibitor combination in mouse cochlear explant cultures. Compounds alone or combination of the compounds were added 1 h before cisplatin (150 μM) to P3 FVB cochlear explants for 24 h, and number of outer hair cells per 160 μm of middle turn regions of the cochlea were counted by phalloidin staining, mean±SEM, P=*<0.05, P=***<0.001, compared to cisplatin alone by unpaired two-tailed Student's t-test. The initial molar ratio between the compounds tested was determined by the ratio given currently to cancer patients (dabrafenib at 150 mg twice daily plus trametinib at 2 mg once daily).

Figure 10A:
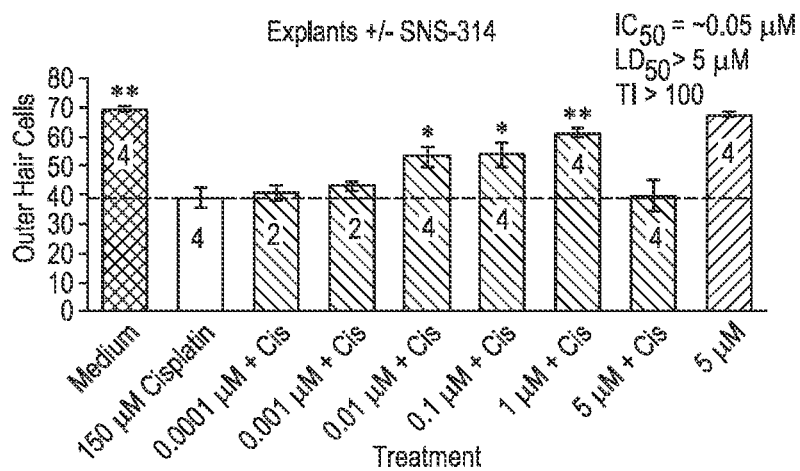
Figure 10B:
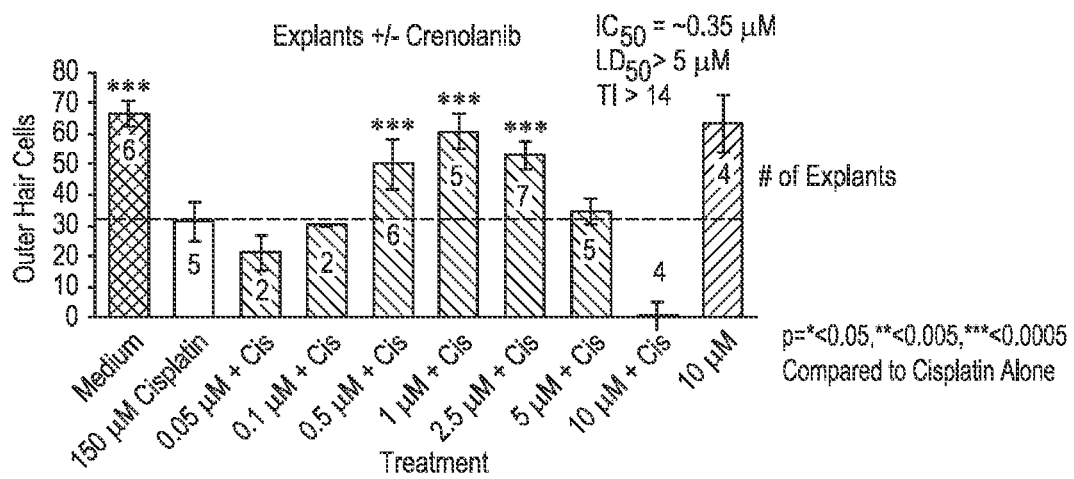

FIGS. 10A and 10B show data from mouse cochlear explants for a number of inhibitors (Mubritinib, SNS-314, and Crenolanib).

EGFR Signaling. Epidermal growth factor receptor (EGFR; ErbB-1; HER1 in humans) is a cell-surface receptor activated by binding of its specific ligands, including epidermal growth factor (EGF), transforming growth factor a (TGFα), HB-EGF, amphiregulin, betacellulin, epigen, and epiregulin. EGFR is a member of the ErbB family of receptors, a subfamily of four closely related receptor tyrosine kinases: EGFR, HER2/c-neu (ErbB-2), Her3 (ErbB-3) and Her4 (ErbB-4). Upon activation by its growth factor ligands, EGFR undergoes a transition from an inactive monomeric form to an active homodimer. In addition to forming homodimers after ligand binding, EGFR can pair with another member of the ErbB receptor family, such as ErbB2/Her2/neu, to create an activated heterodimer. EGFR dimerization stimulates its intrinsic intracellular protein-tyrosine kinase activity. As a result, autophosphorylation of several tyrosine (Y) residues in the C-terminal domain of EGFR occurs. These include Y992, Y1045, Y1068, Y1148 and Y1173. This autophosphorylation elicits downstream activation, signaling and/or expression of Ras/Raf/MEK/ ERK/MAPK, JAK/STAT, PI3K/AKT/mTOR, NCK-PAK-JNK, PLC-DAG-PKC and/or a number of cell cycle-associated protein kinase proteins/pathways. These signaling events initiate several signal transduction cascades leading to DNA synthesis and cell migration, adhesion, and proliferation. Accordingly, "EGFR signaling" or "an EGFR signaling pathway" refers herein to signaling by EGFR itself, as well as the Ras/Raf/MEK/ERK/MAPK, JAK/STAT, PI3K/AKT/mTOR, NCK-PAK-JNK, PLC-DAG-PKC, cell cycle-associated protein kinase pathways/proteins downstream thereof.

Ras/Raf/MEK/ERK/MAPK Pathway. The Ras/Raf/MEK/ ERK/MAPK pathway (also known as the MAPK/ERK pathway) is well-known in the art and plays a central role in regulating mammalian cell growth by relaying extracellular signals from ligand-bound cell surface tyrosine kinase receptors such as EGFR. Activation of the MAPK/ERK (mitogen-activated protein kinase/extracellular signal-regulated kinase) pathway is via a cascade of phosphorylation events that begins with activation of Ras, e.g., HRas (GENBANK Accession No. NP_001123914, NP_001304983, or NP_789765), KRas (GENBANK Accession No. NP_004976 or NP_203524) or NRas (GENBANK Accession No. NP_002515). Activation of Ras leads to the recruitment and activation of Raf, e.g., c-Raf or Raf-1 (GENBANK Accession No. NP_002871), A-Raf (GENBANK Accession No. NP_001243125, NP_001645 or NP_001243126) or B-Raf (GENBANK Accession No. NP_004324). Activated Raf then phosphorylates and activates MEK1/2 (i.e., MAPK/ERK Kinase-1 and -2; GENBANK Accession Nos. NP_002746 and NP_109587, respectively), which then phosphorylates and activates ERK1/2 (i.e., MAPK3/MAPK1; UniProt Accession Nos. P28482 and P27361, respectively). This chain of proteins, from Ras to ERK, communicates signals from cell-surface receptors to the DNA. ERK generates extensive changes in gene expression mediated by transcription factors that control cell cycle progression, differentiation, protein synthesis, metabolism, cell survival, cell migration, and invasion and senescence.

JAK/STAT Pathway. The Janus kinase/signal transducers and activators of transcription (JAK/STAT) pathway stimulates cell proliferation, differentiation, cell migration and apoptosis. Mechanistically, JAK/STAT signaling is composed of a few principal components. In mammals, the JAK family includes four members: JAK1 (GENBANK Accession No. NP_001307852), JAK2 (GENBANK Accession No. NP_001309123 or NP_001309127), JAK3 (GENBANK Accession No. NP_000206) and Tyk2 (GENBANK Accession No. NP_003322). JAK activation occurs upon ligand-mediated receptor multimerization thereby allowing trans-phosphorylation. The activated JAKs subsequently phosphorylate additional targets, in particular STATs. STATs are latent transcription factors that reside in the cytoplasm until activated. The mammalian STATs (i.e., STAT1, GENBANK Accession No. NP_009330 or NP_644671; STAT2, GENBANK Accession No. NP_005410 or NP_938146; STAT3, GENBANK Accession No. NP_003141, NP_644805, or NP_998827; STAT4, GENBANK Accession No. NP_001230764 or NP_003142; STAT5A, GENBANK Accession No. NP_001275647, NP_001275648, or NP_001275649; STAT5B, GENBANK Accession No. NP_036580; and STAT6, GENBANK Accession No. NP_001171549, NP_001171550, NP_001171551 or NP_001171552) bear a conserved tyrosine residue near the C-terminus that is phosphorylated by JAKs. This phosphotyrosine permits the dimerization of STATs through interaction with a conserved SH2 domain. Phosphorylated STATs enter the nucleus and bind specific regulatory sequences to activate or repress transcription of target genes. Thus, the JAK/STAT cascade provides a direct mechanism to translate an extracellular signal into a transcriptional response.

PI3K/AKT/mTOR Pathway. The PI3K/AKT/mTOR pathway is an intracellular signaling pathway important in regulating the cell cycle. Ligand-bound activation of EGFR leads to the activation of PI3K (phosphatidylinositol-4,5-bisphosphate 3-kinase, e.g., Class 1 enzymes such as PIK3CA, PIK3CB, PIK3CG, PIK3CD, PIK3R1, PIK3R2, PIK3R3, PIK3R4, PIK3R5 and PIK3R6; Class 2 enzymes such as PIK3C2A, PIK3C2B and PIK3C2G; and Class enzyme PIK3C3). PI3K subsequently phosphorylates Akt (i.e., Protein Kinase B or PKB including AKT1, UniProt Accession No. P31749; AKT2, UniProt Accession No. P31751; and AKT3, UniProt Accession No. Q9Y243). PIK3 subsequently activates mTOR complexes, mTORC1 and mTORC2, which are each involved in cell growth. mTORC1, which is composed of mTOR, Raptor, GβL (mammalian lethal with SEC13 protein 8) and domain-containing mTOR-interacting protein (DEPTOR), unifies multiple signals that indicate the availability of growth factors, nutrients and energy in order to promote cellular growth and catabolic processes during stress. Active mTORC1 exerts numerous downstream biological effects, including the translation of mRNA by phosphorylating downstream targets, such as 4E-BP1 and p70 S6 kinase, the suppression of autophagy through Atg13 and ULK1, ribosome biogenesis, and activation of transcription that leads to increased mitochondrial activity or adipogenesis. mTORC2, which is composed of mTOR, Rictor, GβL, Sin1, PRR5/Protor-1 and DEPTOR, promotes cell survival through the activation of Akt. mTORC2 regulates cytoskeletal dynamics, ion transport and growth by activating PKCα and phosphorylating SGK1.

NCK-PAK-JNK Pathway. Nck (non-catalytic region of tyrosine kinase adaptor protein 1; GENBANK Accession No. NP_001177725 or NP_001278928) is known to bind to activated EGFR through its SH2 domain. Nck associates with PAK1 (p21/CDC42/Rac1-Activated Kinase-1; GENBANK Accession No. NP_001122092 or NP_002567) through the first N-terminal polyproline domain of PAK1 and an SH3 domain of Nck. Nck activates PAK, which subsequently activates JNKs (c-Jun Kinases) via MEKK1 (MAP/ERK Kinase Kinase-1; GENBANK Accession No. NP_005912) and MKK4/7 (MAP Kinase Kinase-4/7; GENBANK Accession No. NP_1268364, NP_003001, NP_001284484, or NP 001284485). Activated JNKs enter the nucleus and cause phosphorylation of transcription factors such as c-Fos and c-Jun.

PLC-DAG-PKC Pathway. Phospholipase C (PLC) ties EGFR activation to the generation of secondary messengers and calcium metabolism. EGFR recruits and phosphorylates PLC-yl (GENBANK Accession No. NP_002651 or NP_877963), which then generates diacylglycerol (DAG) and inositol-1,4,5-trisphosphate (IP3) from Ptdlns(4,5)P2. DAG activates many isoforms of Protein kinase C (PKC), including conventional isoforms α, β, and γ, as well as PKC-ε and PKC-θ. PKC-α, PKC-β, PKC-γ, and PKC-ε phosphorylate and activate c-Raf-1, thereby amplifying HRas/MEK1 and MEK2/ERK1/2 kinase cascades. PKC-θ activates Nuclear factor NF-kappa-B inhibitor kinase beta (IKK-beta) resulting in activation of the Nuclear factor NF-kappa-B (NF-kB).

Cell Cycle-Associated Protein Kinases. Protein kinases downstream or interacting with EGFR play a central role in the regulation of the eukaryotic cell cycle. More specifically, these protein kinases are involved in signal transduction, chromosome condensation, centrosome maturation, spindle assembly, spindle orientation, meiotic maturation, and cytokinesis. Accordingly, a "cell-cycle associated protein kinase" refers to a kinase downstream of, or interacting with, EGFR that regulates one or more of cell cycle progression, cell division, cell proliferation, and cell cycle machinery. In certain embodiments, the cell cycle-associated protein kinase of this invention is Her2/neu, Aurora kinase, B-raf (as discussed herein) or platelet-derived growth factor receptor (PDGFR).

Her2/neu Kinase. Her2/neu is a 185-kDa transmembrane protein (GENBANK Accession No. NP_001005862, NP_001276865, NP_001276866, NP_001276867, or NP_004439) encoded by the erbB2 oncogene located on chromosome 17q21-22. Normal expression of Her2/neu at the cell surface is essential for regulating cell growth and epithelial cell survival. While a natural ligand of Her2/neu has not been identified, Her2/neu is known to be a preferred dimerization partner forming potent heterodimers with EGFR and Her3 (Lenferink, et al. (1998) *EMBO J.* 17:3385-97).

Aurora Kinase. The Aurora kinases are a family of highly conserved serine/threonine kinases that are important for faithful transition through mitosis (Bischoff, et al. (1998) *EMBO J.* 17:3052-65; Carmena & Earnshaw (2003) *Nat. Rev. Mol. Cell Biol.* 4:842-54; Giet & Prigent (1999) *J. Cell Sci.* 112:3591-601). The gene for Aurora A, maps to chromosome region 20q13.2, a region that has been found amplified in different human cancers. Aurora A (GENBANK Accession No. NP_001310232, NP_001310233, NP_001310234, NP_003591 or NP_940835) plays an important role in centrosome maturation, spindle assembly, meiotic maturation, and metaphase I spindle orientation (Carmena & Earnshaw (2003) *Nat. Rev. Mol. Cell Biol.* 4:842-54). Aurora A function is regulated by degradation, phosphorylation, and dephosphorylation, with its kinase activity dependent upon phosphorylation of threonine 288 (Thr288) in the activation loop. Selective inhibition of Aurora A results in inhibition of autophosphorylation of Aurora A at Thr288, monopolar spindles, and G2-M arrest (Girdler, et al. (2006) *J. Cell Sci.* 119:3664-75; Carpinelli & Moll (2008) *Expert Opin. Ther. Targets* 12:69-80). The Aurora B (GENBANK Accession No. NP_001243763, NP_001271455, NP_001300879, NP_001300880, or NP_001300881) gene maps to chromosome region 17p13.1 and this kinase forms part of the chromosomal passenger complex (CPC) with three non-enzymatic subunits: inner centromere protein (INCENP), Survivin, and Borealin (Vader, et al. (2006) *J. Cell Biol.* 173:833-7). The highly dynamic CPC is critical for chromosome condensation, chromosome orientation on the mitotic spindle, through correcting chromosome-microtubule attachment errors, and the spindle-assembly checkpoint (SAC), as well as the final stages of cytokinesis (Sampath, et al. (2004) Cell 118:187-20; Terada, et al. (1998) EMBO J. 17:667-76; Carmena, et al. (2012) *Nat. Rev. Mol. Cell Biol.* 13:789-803; Tanenbaum, et al. (2011) *Curr. Biol.* 21:1356-6). Aurora C (GENBANK Accession No. NP_001015878, NP_001015879, or NP_003151) expression has been reported in testis, thyroid, and placenta and in meiotically dividing gametes (Ulisse, et al. (2006) *Int. J. Cancer* 119:275-82; Bernard, et al. (1998) *Genomics* 53:406-9; Kimura, et al. (1999) *J. Biol. Chem.* 274:7334-40; Yang, et al. (2010) *Mol. Biol. Cell* 21:2371-83). Further, nuclear EGFR, associated with STAT5, has been shown to bind and increase Aurora-A gene expression (Hung, et al. (2008) *Nucl. Acids Res.* 36(13):4337-51). Overexpression of Aurora C has been suggested to induce abnormal cell division resulting in centrosome amplification and multinucleation in cells.

PDGFR Kinase. PDGFR is involved in the control of cell proliferation, differentiation and survival in various tissues of vertebrates. Activated PDGFR phosphorylates itself and other proteins, and thereby engages intracellular signaling pathways that trigger cellular responses such as migration and proliferation. PDGFRα (UniProtKB Accession No. P16234) and PDGFRβ (GENBANK Accession No. NP_002600) are highly expressed in the rapidly growing otocyst on embryonic days 12-14 and weakly expressed thereafter (Lee, et al. (2004) *Acta Oto-Laryng.* 124:558-62). Based upon this analysis, it was suggested that integrity of PDGF signaling is required for the proliferation of developing cochlear hair cells (Lee, et al. (2004) *Acta Oto-Laryng.* 124:558-62). In addition, previous studies have suggested that PDGF signaling is required for the trophism of the vascular and mesenchymal compartment in the neonatal mouse inner ear and, indirectly, for the survival of the sensory epithelium (Hayashi, et al. (2008) *Hear. Res.* 245:73-81). Notably, heterodimerization and cross talk between the PDGFRβ and the EGFR has indicated a role for EGFR transactivation in PDGF-stimulated cell migration (Saito, et al. (2001) *Mol. Cell Biol.* 21(19):6387-94).

Inhibitors of EGFR Signaling. An inhibitor of EGFR signaling is intended to refer to any molecule that reduces, blocks or decreases the expression or activity of an EGFR protein or a protein that interacts with or is in a downstream pathway of EGFR, e.g., a Ras, Raf, MEK, ERK/MAPK, JAK, STAT, PI3K, AKT, mTOR (including a protein of an mTOR complex), NCK, PAK, JNK, PLC, PKC or cell cycle-associated protein kinase (e.g., Her-2, Aurora kinase, B-Raf, or PDGFR). An inhibitor of EGFR signaling also includes an inhibitor that blocks the expression or activity of an EGFR ligand such as EGF, TGF-α, HB-EGF, AR, BTC, EPR, or epigen. In certain embodiments, the inhibitor of EGFR signaling inhibits or reduces the expression or activity of EGFR, PLC, STATS, JAK2, PI3K, MEK, Her-2, Aurora kinase, B-Raf, or PDGFR.

An inhibitor of this invention can selectively decrease or block the expression of an EGFR signaling protein (i.e., transcription or translation of the protein), decrease or block the activity of an EGFR signaling protein (i.e., binding to ligands, tyrosine kinase activity, phosphorylation, protein-protein interactions, and/or downstream signaling), decrease or block the biological effect(s) of an EGFR signaling protein, and/or modify half-life or subcellular localization (membrane versus cytoplasmic or nuclear localization, internalization, and recycling) of an EGFR signaling protein. In particular, an inhibitor of EGFR signaling is an active agent that selectively decreases or blocks one or more of the following: transcription or translation, ligand binding, phosphorylation, multimerization, tyrosine kinase activity, internalization, and/or translocation into the nucleus.

Ideally, EGFR signaling is completely blocked, or is reduced by at least 10%, at least 20%, at least 30%, at least 40%, at least 50%, at least 60%, at least 70%, at least 75%, at least 80%, at least 85%, at least 90%, at least 92.5%, at least 95%, at least 97%, at least 98%, at least 98.5%, at least 99%, at least 99.25%, at least 99.5%, or at least 99.75% by the inhibitor of EGFR signaling inhibitor as compared to normal physiologic levels.

The inhibitor of EGFR signaling of this invention typically has a half maximal (50%) inhibitory concentration ($IC_{50}$) in the range of 1 µM to 100 µM. Preferably, the inhibitor of EGFR signaling has an $IC_{50}$ value of less than 10 µM, less than 5 µM, less than 1 µM, or less than 100 nM. Moreover, in some embodiments, the inhibitor of EGFR signaling is specific/selective for one or more of the EGFR signaling proteins of interest and fails to inhibit, or inhibits to a substantially lesser degree other non-EGFR pathway proteins. In this respect, it is preferable that the inhibitor of EGFR signaling is a selective inhibitor of EGFR signaling. Preferably, selectivity is for one, two, three or four EGFR signaling proteins and fails to inhibit, or inhibits to a substantially lesser degree other non-EGFR pathway proteins. By way of illustration, an inhibitor can be a dual EGFR and ERBB2 inhibitor, both of which are EGFR signaling proteins. Methods for assessing the selectively of inhibitors are known in the art and can be based upon any conventional assay including, but not limited to the determination of the $IC_{50}$, the binding affinity of the inhibitor (i.e., $K_i$), and/or the half maximal effective concentration ($EC_{50}$) of the inhibitor for EGFR signaling protein of interest as compared to another protein (comparative protein). In particular embodiments, a selective inhibitor of EGFR signaling is an inhibitor that has an $IC_{50}$ value for an EGFR signaling protein of interest that is at least twice or, more desirably, at least three, four, five, or six times lower than the corresponding $IC_{50}$ value for a comparative protein. Most desirably, a selective inhibitor of EGFR signaling has an $IC_{50}$ value for an EGFR signaling protein which is at least one order of magnitude or at least two orders of magnitude lower than the $IC_{50}$ value for a comparative protein.

An inhibitor of this invention can be a nucleic acid-based inhibitor such as an inhibitory RNA molecule (e.g., antisense molecule, a ribozyme, siRNA, shRNA, miRNA, etc.); a protein that affects splicing or 3' processing (e.g., polyadenylation), or the level of expression of another gene within the cell (i.e., where gene expression is broadly considered to include all steps from initiation of transcription through production of a process protein), such as by mediating an altered rate of mRNA accumulation or transport or an alteration in post-transcriptional regulation; an antibody (including fragments or mimetics); a peptide; a small organic molecule; or a combination thereof.

The term siRNA refers to double stranded RNA or RNA and DNA species that are active to reduce expression of targeted gene. These molecules are known variously as "small interfering RNA," "short interfering RNA" or "silencing RNA." siRNA strands are usually 20-25 nucleotides long, although larger precursor molecules which are subject to cleavage in vivo to form the active species are within the scope of the term as used herein.

As used herein, an "miRNA molecule" or "miRNA" is a small RNA molecule, typically about 20 to 25 nucleotides, encoded by the genome of an animal or produced synthetically with a sequence which corresponds to one encoded by the genome of the animal. As used herein, miRNA molecules may be single-stranded or double-stranded.

When the inhibitor is, e.g., an inhibitory RNA, peptide or protein, nucleic acid molecules encoding such an inhibitor can be carried by the same nucleic acid molecule that encodes the EGFR inhibitor or can be a separate nucleic acid molecule present on the same expression vector or part of a different expression vector. Inhibitory RNA molecules can be readily prepared based upon the nucleic acid sequences disclosed herein. Alternatively, inhibitory RNA molecules such as siRNAs can be obtained from commercial sources such as Dharmacon (see, e.g., ON-TARGET plus siRNA SMART pools), Invitrogen or Zyagen. A decrease in the expression of a protein can be measured using conventional techniques such as dot blot, northern blot, ELISA or western blot analysis.

EGFR Inhibitors. EGFR inhibitors that selectively decrease or block the expression of EGFR itself include, but are not limited to, EGFR antisense, siRNA and miRNA molecules. Exemplary antisense and siRNA that reduce the expression of EGFR are disclosed, e.g., in US 2011/0046067 and Kang, et al. (2006) Cancer Gene Ther. 13(5):530-8. Exemplary miRNA that reduce the expression of EGFR are disclosed, e.g., in U.S. Pat. No. 8,673,872, incorporated herein by reference in its entirety.

An EGFR inhibitor can also be an antibody, antibody fragment, or antibody mimetic that specifically binds EGFR and antagonizes the activity thereof by, e.g., blocking ligand binding, activation, phosphorylation or protein-protein interactions. Cetuximab (IgG1) and Panitumumab (IgG2) are examples of monoclonal antibody inhibitors of EGFR. Other antagonistic monoclonal antibodies include Zalutumumab, Nimotuzumab, MaLuzumutab, ICR62, and mAb806. See U.S. Pat. Nos. 6,506,883, 6,235,883, 5,891,996, 4,943,533, WO 2004/056847, WO 2002/092771, WO 2002/66058, and WO 1995/20045. Such antibodies block the extracellular ligand binding domain thereby blocking tyrosine kinase activation.

Peptide inhibitors of EGFR that regulate EGFR multimerization and activation are also of use in this invention. Exemplary peptide inhibitors of EGFR can be based upon the following juxtamembrane sequence from EGFR: LLL-WALGIGLFMRRRHIVRKRTLRRLLQERELVEPLTPS (SEQ ID NO:1) and may optionally include a cell penetrating component such as a protein transduction domain (PTD) to facilitate delivery into the cell. See US 2016/0311884.

Still further, the EGFR inhibitor can be small molecule that inhibits the tyrosine kinase activity of EGFR. Without kinase activity, EGFR is unable to activate itself, which is a prerequisite for binding of downstream adaptor proteins. Examples of small molecule inhibitors of EGFR include, but are not limited to, erlotinib (CAS 183321-74-6), gefitinib (CAS 184475-35-2), lapatinib (CAS 231277-92-2, dual EGFR and ERBB2 inhibitor), neratinib (CAS 698387-09-6), canertinib (CAS 267243-28-7), vandetanib (CAS 443913-73-3), afatinib (CAS 439081-18-2), AG 1478 (CAS 153436-53-4), TAK-285 (CAS 871026-44-7, dual HER2 and EGFR inhibitor), ARRY334543 (CAS 845272-21-1, dual EGFR phosphorylation inhibitor), Dacomitinib (CAS 1110813-31-4, EGFR and ERBB2 inhibitor), AZD3759 (CAS 1626387-80-1), NT113 (CAS 1398833-56-1, pan-ERBB inhibitor), OSI-420 (Desmethyl Erlotinib, CAS 183321-86-0, EGFR inhibitor), AZD8931 (CAS 848942-61-9, EGFR, HER2 and HERS inhibitor), AEE788 (CAS 497839-62-9, EGFR, HER2 and VEGFR 1/2 inhibitor), Pelitinib (EKB-569, CAS 257933-82-7, pan-ErbB inhibitor), CUDC-101 (CAS 1012054-59-9, EGFR, HER2 and HDAC inhibitor), XL647 (CAS 651031-01-5, dual HER2 and EGFR inhibitor), BMS-599626 (CAS 714971-09-2, dual EGFR and HER2 inhibitor), PKC412 (CAS 120685-11-2, EGFR, PKC, cyclic AMP-dependent protein kinase and S6 kinase inhibitor), BIBX1382 (CAS 196612-93-8, EGFR inhibitor) and AP26113 (CAS 1197953-54-0, ALK and EGFR inhibitor), and derivatives and combinations thereof. In some embodiments, the EGFR inhibitor is not Pelitinib.

Ras/Raf/MEK/ERK/MAPK Inhibitors. Inhibitors of this pathway that selectively decrease or block the expression of Ras, Raf, MEK, ERK/MAPK include, but are not limited to, antisense, siRNA and miRNA molecules. By way of illustration, antisense inhibition of MEK1 is disclosed in U.S. Pat. No. 6,096,543, incorporated herein by reference in its entirety.

Examples of Ras inhibitors include, but are not limited to, R115777 (CAS 192185-72-1), BMS-214662 (CAS 195987-41-8), SCH66336 (CAS 193275-84-2), FTI-277 (CAS 1217447-06-7), manumycin A (CAS 52665-74-4), FTI-276 (CAS 170006-72-1), RasCAAX (a peptidomimetic), L-744, 832 (CAS 1177806-11-9), and derivatives and combinations thereof.

Raf inhibitors of use in this invention include, but are not limited to, Bay43-9006 (sorafenib, CAS 284461-73-0, selective inhibitor for B-Raf and C-Raf), vemurafenib (CAS 918504-65-1, B-Raf inhibitor), dabrafenib (CAS 1195764-45-7, B-Raf inhibitor; see also U.S. Pat. Nos. 7,994,185 and 8,415,345), LY3009120 (CAS 1454682-72-4, pan-Raf inhibitor), GW 5074 (CAS 220904-83-6, C-Raf-1 inhibitor), ZM 336372 (CAS 208260-29-1, Raf-1 inhibitor), 2-bromoaldisine (CAS 96562-96-8, RAF/MEK-1/MAPK pathway inhibitor), L-779,450 (CAS 303727-31-3), AZ628 (CAS 878739-06-1, Raf-1 inhibitor), RAF265 (CAS 927880-90-8, B-Raf and VEGFR-2 inhibitor), encorafenib (LGX818, CAS 1269440-17-6, B-Raf inhibitor), and derivatives and combinations thereof.

MEK inhibitors include, but are not limited to, SL-327 (CAS 305350-87-2, inhibitor of MEK1 and MEK2), PD 184,352 (CAS 212631-79-3), 2-bromoaldisine (CAS 96562-96-8, Raf/MEK-1/MAPK pathway inhibitor), PD 198306 (CAS 212631-61-3, non-ATP-competitive inhibitor of MEK1/2), PD 0325901 (CAS 391210-10-9, inhibitor of MEK and suppressor of ERK phosphorylation), MEK inhibitor II (CAS 623163-52-0), PD 184161 (CAS 212631-67-9, selective inhibitor for MEK1 and MEK2), U-0126 (CAS 109511-58-2, inhibitor for MEK1/2), PD 98059 (CAS 167869-21-8, selective inhibitor for MEK1), AS703026 (CAS 1236699-92-5, inhibitor for MEK1/2), BAY 869766 (CAS 923032-37-5, non-ATP-competitive inhibitor of MEK-1 and MEK-2), PD 318088 (CAS 391210-00-7, inhibitor for MEK1/2), selumetinib (CAS 606143-52-6, MEK-1 non-ATP competitive inhibitor), TAK-733 (CAS 1035555-63-5, allosteric inhibitor of MEK), Trametinib (CAS 871700-17-3, allosteric inhibitor of MEK1/MEK2), and derivatives and combinations thereof. See also WO 1998/037881, WO 1999/901426, WO 2000/041505, WO 2000/041994, WO 2000/042002, WO 2000/042003, WO 2000/042022, WO 2000/042029, WO 2001/068619, and WO 2002/036570 for additional MEK inhibitors.

ERK inhibitors include, for example, SCH772984 (CAS 942183-800-4, ERK1/2 inhibitor), DEL-22379 (CAS 181223-80-3, ERK dimerization inhibitor), VX-11e (CAS 896720-20-0, ERK2 inhibitor), Pluripotin (SC1, CAS 839707-37-8, dual ERK1 and RasGAP inhibitor), Ulixertinib (BVD-523, VRT752271, CAS 869886-67-9, ERK1/ERK2 inhibitor), FR 180204 (CAS 865362-74-9, ATP-competitive ERK inhibitor), GDC-0994 (CAS 1453848-26-4, ERK1/2 inhibitor), KO-947 (Kura Oncology, ERK1/2 inhibitor), and derivatives and combinations thereof. See also JP 2005-330265 for additional ERK inhibitors.

JAK/STAT Inhibitors. Inhibitors that selectively decrease or block the expression of JAK or STAT include, but are not limited to, antisense, siRNA and miRNA molecules. By way of illustration, antisense inhibition of STAT-2, STAT-3, STAT-4, STAT-5 and STAT-6 is disclosed in US 2004/0101853, U.S. Pat. Nos. 6,159,694, 6,479,465, 8,722,873 and WO 1998/040478, respectively. Likewise, siRNA for reducing the expression of STAT-1 and STAT-2 are disclosed in U.S. Pat. No. 9,198,911. STAT-3 siRNA are described in US 2010/0298409, STAT-5 siRNA are described in WO 2009/039199, and STAT-6 siRNA are described in U.S. Pat. No. 7,566,700. SiRNA molecules of use in inhibiting the expression of Jak1 and Jak3 are disclosed in U.S. Pat. No. 9,198,911, incorporated herein by reference in its entirety.

Non-limiting examples of STAT inhibitors include, but are not limited to, WP-1034 (CAS 857064-42-7, Jak-Stat inhibitor), fludarabine (CAS 21679-14-1, STAT1 inhibitor), S3I-201 (CAS 501919-59-1, inhibitor of STAT3 DNA-binding activity), Stattic (CAS 19983-44-9, STAT3 inhibitor), APTSTAT3-9R (STAT-binding peptide), STA-21 (CAS 28882-53-3, STAT3 inhibitor), SH-4-54 (CAS 1456632-40-8), Napabucasin (CAS 83280-65-3, STAT3 inhibitor), Cryptotanshinone (CAS 35825-57-1, STAT3 inhibitor), niclosamide (CAS 50-65-7, STAT3 inhibitor), NSC 74859 (CAS 501919-59-1, STAT3 inhibitor), HO-3867 (CAS 1172133-28-6, STAT3 inhibitor), and derivatives and combinations thereof.

Jak1/Jak2 inhibitors include, but are not limited to, AG-490 (CAS 133550-30-8), CYT387 (CAS 1056634-68-4), SB1518 (Pacritinib, CAS 937272-79-2), LY3009104 (INCB28050, Baricitinib, CAS 1187594-09-7), TG101348 (CAS 936091-26-8), BMS-911543 (CAS 1271022-90-2), AZD1480 (CAS 935666-88-9), Ruxolitinib (INCB018424, CAS 941678-49-5), CEP-701 (CAS 111358-88-4), TG101348 (Fedratinib, CAS 936091-26-8), SD 1008 (CAS 960201-81-4, JAK2/STAT3 inhibitor), WP-1066 (CAS 857064-38-1, JAK2/STAT3 inhibitor), and derivatives and combinations thereof. JAK3 inhibitors include, but are not limited to, Janex 1 (WHI-P131, CAS 202475-60-3), PF-956980 (CAS 1262832-74-5), WHI-P154 (CAS 211555-04-3), VX-509 (Decernotinib, CAS 944842-54-0), JAK3 Inhibitor IV (ZM-39923, CAS 1021868-92-7), tofacitinib (CP-690550, CAS 540737-29-9), and derivatives and combinations thereof.

PI3K/AKT/mTOR Inhibitors. Inhibitors that selectively decrease or block the expression of PI3K, AKT or mTOR include, but are not limited to, antisense, siRNA and miRNA molecules. By way of illustration, siRNA inhibition of PI3K, AKT and mTOR is disclosed in, e.g., US 2005/0272682, US 2008/0161547, and U.S. Pat. No. 9,012,622 respectively.

Small molecules of use in inhibiting PI3K include, but are not limited to, SF1101 (LY 294002, CAS 154447-36-6), BKM120 (CAS 944396-07-0), BYL719 (CAS 1217486-61-7), XL-147 (CAS 956958-53-5), ZSTK-474 (CAS 475110-96-4), PX-866 (CAS 502632-66-8), PI-103 (CAS 371935-74-9), and derivatives and combinations thereof.

Exemplary AKT inhibitors include, e.g., AZD5363 (CAS 1143532-39-1), GDC-0068 (CAS 1001264-89-6, ATP-competitive pan-Akt inhibitor), MK-2206 (CAS 1032350-13-2), Perifosine (CAS 157716-52-4), PBI-05204 (Oleandrin, CAS 465-16-7), GSK2141795 (CAS 1047634-65-0), and SR13668 (CAS 637774-61-9), and derivatives and combinations thereof. Additional AKT inhibitors are described in US 2010/0009397, US 2007/0185152, U.S. Pat. Nos. 6,960,584, 7,098,208, 7,223,738, 7,304,063, 7,378,403, 7,396,832, 7,399,764, 7,414,055, 7,544,677, 7,576,209, 7,579,355, 7,589,068, 7,638,530, 7,655,649, 7,705,014, 7,750,151, 7,943,732, 8,003,643, 8,003,651, 8,008,317, 8,168,652, 8,263,357, 8,273,782, and 8,324,221.

Exemplary dual mTOR/PI3K inhibitors include, e.g., SF1126 (CAS 936487-67-1), BEZ235 (CAS 915019-65-7), BGT-226 (CAS 1245537-68-1), PF-04691502 (CAS 1013101-36-4), GNE-477 (CAS 1032754-81-6), XL765 (CAS 1349796-36-6), GDC-0941 (CAS 957054-30-7), GDC-0980 (CAS 1032754-93-0), PF-05212384 (CAS 1197160-78-3), and derivatives and combinations thereof.

Inhibition of mTOR can be achieved using one or more of the following inhibitors, e.g., OSI-027 (CAS 936890-98-1), INK-128 (CAS 1224844-38-5), AZD-8055 (CAS 1009298-09-2), AZD-2014 (CAS 1009298-59-2), Palomid 529 (CAS 914913-88-5), Pp-242 (CAS 1092351-67-1), GSK2126458 (CAS 1086062-66-9), PF-04691502 (CAS 1013101-36-4), wortmannin (CAS 19545-26-7), Ku-0063794 (CAS 938440-64-3), WAY-600 (CAS 1062159-35-6), WYE-687 (CAS 1062161-90-3), WYE-354 (CAS 1062169-56-5), rapamycin (CAS 53123-88-9), and derivatives and combinations thereof. Rapamycin derivatives are further described in, e.g., U.S. Pat. Nos. 5,258,389, 5,100,883, 5,118,678, 5,151,413, 5,256,790, 5,120,842, US 2011/0178070, WO 1994/09010, WO 1992/05179, WO 1993/11130, WO 1994/02136, WO 1994/02485, WO 1994/02136, WO 1995/16691, WO 1996/41807, WO 1996/41807, WO 1998/02441, WO 2001/14387, and WO 1995/14023. See also US 2016/0244424 for additional PI3K/AKT/mTOR inhibitors.

NCK-PAK-JNK Inhibitors. Inhibitors that selectively decrease or block the expression of NCK, PAK or JNK include, but are not limited to, antisense, siRNA and miRNA molecules. By way of illustration, siRNA inhibition of Pak1 is disclosed in, e.g., WO 2013/135745. Similarly, siRNA inhibition of JNK1, JNK2 and JNK3 is disclosed in, e.g., US 2015/0361184.

Inhibitors of PAK kinases are known in the art and include, but are not limited to, 2-aminopyrido[2,3-d]pyrimidin-7(8H)-ones such as those disclosed in WO 2009/086204, WO 2010/071846, WO 2011/044535, WO 2011/156646, WO 2011/156786, WO 2011/156640, WO 2011/156780, WO 2011/156775, and WO 2011/044264; 1H-thieno[3,2-c]pyrazoles, 3-amino-tetrahydropyrrolo[3,4-c]pyrazoles and N4-(1H-pyrazol-3-yl)pyrimidine-2,4-diamines as disclosed in WO 2004/007504, WO 2007/023382, WO 2007/072153, and WO 2006/072831; N2-bicyclic indolyl, indazolyl and benzimidazolyl derivatives of N4-(1H-pyrazol-3-yl)pyrimidine-2,4-diamines as described in U.S. Pat. No. 8,637,537; PF-3758309 (CAS 898044-15-0); IPA-3 (CAS 42521-82-4); FRAX597 (CAS 1286739-19-2); FRAX486 (CAS 1232030-35-1); FRAX1036 (CAS 1432908-05-8); and derivatives and combinations thereof.

Non-limiting examples of JNK1, JNK2 and/or JNK3 inhibitors include, but are not limited to, JNK Inhibitor V (CAS 345987-15-7), JNK Inhibitor VII (TAT-TI-JIPi$_{53-163}$, CAS 305350-87-2), JNK Inhibitor VIII (CAS 894804-07-0), JNK-IN-7 (CAS 1408064-71-0), JNK Inhibitor IX (CAS 312917-14-9), JNK Inhibitor XI (CAS 2207-44-5), JNK Inhibitor XVI (CAS 1410880-22-6), AEG 3482 (CAS 63735-71-7), doramapimod (CAS 285983-48-4, p38a MAPK and JNK2 inhibitor), CC-401 (CAS 395104-30-0), SP600125 (CAS 129-56-6), AS601245 (CAS 345987-15-7), and derivatives and combinations thereof. In some embodiments, the inhibitor is not leflunomide.

PLC-DAG-PKC Inhibitors. Inhibitors that selectively decrease or block the expression of PLC or PKC include, but are not limited to, antisense, siRNA and miRNA molecules. By way of illustration, siRNA inhibition of PLC is disclosed in U.S. Pat. No. 9,546,367, the siRNA molecules of which are incorporated herein by reference.

Anti-PLCγ antibodies are also known in the art for use in modulating the binding and/or catalytic activity of a PLCγ. Examples of anti-PLCγ antibodies are described in, for example, Lee, et al. (2002) *Mol. Vis.* 8:17-25 and Buckley, et al. (2004) *J. Biol. Chem.* 279:41807-14.

Examples of small molecule inhibitors of PLC include, but are not limited to, D609 (CAS 83373-60-8), edelfosine (ET-18-OCH3, CAS 77286-66-9, dual PLC/PKC inhibitor), manoalide (CAS 75088-80-1), NCDC (CAS 10556-88-4), U-73122 (CAS 112648-68-7), and derivatives and combinations thereof.

Her2/neu Inhibitors. Inhibitors that selectively decrease or block the expression of Her2/neu include, but are not limited to, antisense, siRNA and miRNA molecules. By way of illustration, siRNA inhibition of Her2/neu is disclosed in, e.g., Faltus, et al. (2004) *Neoplasia* 6(6):786-95; *Choudhury*, et al. (2004) *Int. J. Cancer* 108:71-77.

Anti-Her2/neu antibodies are also known in the art for use in modulating the activity of Her2/neu. Examples of anti-Her2/neu antibodies include, but are not limited to, trastuzumab (HERCEPTIN, CAS 180288-69-1) and pertuzumab (PERJETA, CAS 380610-27-5). See Schroeder, et al. (2014) *Molecules* 19:15196-15212 for review.

Examples of small molecule inhibitors of Her2/neu include, but are not limited to, Lapatinib (TYKERP, CAS 231277-92-2, dual EGFR/Her2 inhibitor), Afatinib (GIOTRIF, CAS 439081-18-2, irreversible pan inhibitor), AZD8931 (CAS 848942-61-0, EGFR/Her2/ErbB3 inhibitor), AST-1306 (CAS 897383-62-9, irreversible EGFR and Her2 inhibitor), AEE-788 (CAS 497839-62-0, a dual EGFR and Her2 kinase inhibitor), CI-1033 (Canertinib, CAS 289499-45-2, EGFR and Her2 inhibitor), TAK-165 (Mubritinib, CAS 366017-09-6, Her2 inhibitor, see U.S. Pat. Nos. 6,716,863 and 7,005,526), CP-724714 (CAS 383432-38-0, Her2 inhibitor), CUDC-101 (CAS 1012054-59-9, irreversible HDAC/EGFR/Her2 inhibitor), TAK-285 (CAS 871026-44-7, dual EGFR/Her2 inhibitor), AC-480 (BMS-599626, CAS 714971-09-2, reversible EGFR/Her2/HER4 inhibitor), PF299804 or PF299 (Dacomitinib, CAS 1110813-31-4, irreversible EGFR/Her2/Her4 inhibitor), and EKB-569 (Perlitinib, CAS 257933-82-7, dual EGFR/Her2 inhibitor), and derivatives and combinations thereof. In certain embodiments, the inhibitor is selective for Her2 and exhibits little or no activity against other kinases.

Aurora Kinase Inhibitors. Inhibitors that selectively decrease or block the expression of an Aurora kinase include, but are not limited to, antisense, siRNA and miRNA molecules. By way of illustration, siRNA inhibition of Aurora kinase is disclosed in, e.g., Tao, et al. (2007) *Br. J. Cancer* 97(12):1664-1672; Umene, et al. (2015) *Int. J. Oncol.* 46(4):1498-1506.

Examples of small molecule inhibitors of Aurora kinase include, but are not limited to, SNS314 Mesylate (CAS 1146618-41-8, pan Aurora inhibitor, see US 2016/0287602, US 2015/0329828 and US 2011/0014191), PHA-680632 (CAS 398493-79-3, pan Aurora inhibitor), VE-465 (Tozasertib, VX-680 or MK0457, CAS 639089-54-6), Barasertib (AZD1152, CAS 722544-51-6, Aurora B kinase inhibitor), Alisertib (MLN8237, CAS 1028486-01-2, Aurora A kinase inhibitor), Danusertib (PHA-739358, CAS 827318-97-8, pan Aurora inhibitor), PF-03814735 (CAS 942487-16-3, dual Aurora A/B inhibitor), AMG 900 (CAS 945595-80-2, pan Aurora inhibitor), and derivatives and combinations thereof. In certain embodiments, the inhibitor is selective for Aurora kinase and exhibits little or no activity against other kinases.

PDGFR Inhibitors. Inhibitors that selectively decrease or block the expression of a PDGFR include, but are not limited to, antisense, siRNA and miRNA molecules. By way of illustration, siRNA inhibition of PDGFR is disclosed in, e.g., Chen, et al. (2008) *Liver Int.* 28(10):1446-1457; Kaulfuβ, et al. (2013) *Oncotarget* 4(7):1037-49; Yeh, et al. (2011) *BMC Cancer* 11:139.

Anti-PDGFR antibodies are also known in the art for use in modulating the activity of PDGFR. Examples of anti-PDGFR antibodies include, but are not limited to, IMC-3G3 (anti-PDGFRα antibody; EP 2100618) and IMC-2C5 (PDGFRβ antibody; Shen, et al. (2009) *Neoplasia* 11(6): 594-604).

Examples of small molecule inhibitors of PDGFR include, but are not limited to, Ki11502 (CAS 347155-76-4), imatinib (GLEEVEC/ST571, CAS 220127-57-1, PDGFRα/BCR-ABL/c-kit inhibitor), Ponatinib (AP24534, CAS 943319-70-8, Abl/PDGFRα/VEGFR2/FGFR1/Src inhibitor), Telatinib (CAS 332012-40-5, VEGFR/c-Kit/PDGFRα inhibitor), Amuvatinib (MP-470, CAS 850879-09-3, c-Kit/PDGFRα/Flt3 inhibitor), Crenolanib (CP-868596, CAS 670220-88-9, selective inhibitor of PDGFRα/β, see U.S. Pat. Nos. 7,071,337, 7,183,414, US 2015/0238479 and US 2010/0016353), Axitinib (CAS 319460-85-0, VEGFR1/VEGFR2/VEGFR3/PDGFRβ/c-Kit inhibitor), CP-673451 (CAS 343787-29-1, inhibitor of PDGFRα/β), Nintedanib (BIBF 1120, CAS 656247-17-5, VEGFR/FGFR/PDGFRα/β inhibitor), Masitinib (CAS 790299-79-5, Kit/PDGFRα/β inhibitor), Sunitinib (SUTENT/SU11248, CAS 557795-19-4, VEGFR2/PDGFRβ inhibitor), TSU-68 (SU6668 or Orantinib, CAS 252916-29-3), Linifanib (ABT-869, CAS 796967-16-3, VEGFR/PDGFR inhibitor), AC 710 (CAS 1351522-04-7, selective PDGFR family inhibitor), DMPQ dihydrochloride (CAS 137206-97-4, PDGFRβ inhibitor), GSK 1363089 (CAS 849217-64-7, PDGFR/MET/VEGFR2/Ron/AXL inhibitor), PD 166285 (CAS 212391-63-4, PDGFRβ/FGFR/Src inhibitor) and Toceranib (CAS 356068-94-5, PDGFR and VEGFR inhibitor), and derivatives and combinations thereof.

Sensory Perception. The invention provides for the modulation of sensory perception in an animal by administering to the inner ear an inhibitor of EGFR signaling and optionally an expression vector (e.g., expression viral vector) harboring a nucleic acid molecule encoding an otoprotective agent. By "modulating sensory perception" it is meant achieving, at least in part, the ability to recognize and adapt to environmental changes. In terms of sensory hair cell function, modulation in sensory perception is associated with the generation or protection of sensory hair cells that convert mechanical stimuli in the inner ear into neural impulses, which are then processed in the brain such that an animal is aware of environmental change, e.g., sound, language, or body/head position. Sensory hair cells are preferably generated in the organ of Corti and/or vestibular apparatus. In the context of prophylaxis, sensory hair cells, which would otherwise be initially or further damaged or lost due to, e.g., ototoxic agents, are protected from damage or loss by the administration of an inhibitor of EGFR signaling and optionally an otoprotective agent.

A change in the ability of a subject to detect sound is readily accomplished through administration of simple hearing tests, such as a tone test commonly administered by an audiologist. In most mammals, a reaction to different frequencies indicates a change in sensory perception. In humans, comprehension of language also is appropriate. For example, it is possible for a subject to hear while being unable to understand speech. A change in perception is indicated by the ability to distinguish different types of acoustic stimuli, such as differentiating language from background noise, and by understanding speech. Speech threshold and discrimination tests are useful for such evaluations.

Evaluation of changes in balance, motion awareness, and/or timing of response to motion stimuli also is achieved using a variety of techniques. Vestibular function also can be measured by comparing the magnitude of response to motion stimulus (gain) or timing of initiation of response (phase). Animals can be tested for Vestibulo-Ocular Reflex (VOR) gain and phase using scleral search coils to evaluate improvements in sensory perception. Electronystagmography (ENG) records eye movements in response to stimuli such as, for instance, moving or flashing lights, body repositioning, fluid movement inside the semicircular canals, and the like. Evaluation of balance during movement using a rotating chair or moving platform also is useful in this respect.

To detect a change in sensory perception, a baseline value is recorded prior to the inventive method using any appropriate sensory test. A subject is reevaluated at an appropriate time period following the inventive method (e.g., 1 hour, 6 hours, 12 hours, 18 hours, 1 day, 3 days, 5 days, 7 days, 14 days, 21 days, 28 days, 2 months, 3 months or more following the inventive method), the results of which are compared to baseline results to determine a change in sensory perception.

Method of Prevention or Treatment. The inventive method promotes the protection and/or generation of sensory hair cells that allow perception of stimuli. Accordingly, this invention provides a method for the prevention, treatment, control, amelioration, or reduction of risk of hearing impairments, loss and disorders by administering to a subject in need of treatment an inhibitor of EGFR signaling and/or one or more otoprotective/regenerative agents. Ideally, the inventive method prophylactically or therapeutically treats an animal for at least one disorder associated with loss, damage, absence of sensory hair cells, such as hearing loss and balance disorders. Hearing loss can be caused by damage of hair cells of the organ of Corti due to bacterial or viral infection, heredity, physical injury, acoustic trauma, ototoxic drugs (e.g., aminoglycoside antibiotic or cisplatin) and the like. While hearing loss is easily identified, balance disorders manifest in a broad variety of complications easily attributable to other ailments. Symptoms of a balance disorder include disorientation, dizziness, vertigo, nausea, blurred vision, clumsiness, and frequent falls. Balance disorders treated by the inventive method preferably involve a peripheral vestibular disorder (i.e., a disturbance in the vestibular apparatus) involving dysfunctional translation of mechanical stimuli into neural impulses due to damage or lack of sensory hair cells.

In one aspect, methods of protecting against or preventing hearing loss or impairment are provided. In accordance with such methods, a subject in need of treatment is administered an effective amount of inhibitor of EGFR signaling. In some embodiments, the inhibitor of EGFR signaling inhibits the expression or activity of EGFR, a Ras/Raf/MEK/ERK/MAPK protein, a JAK/STAT protein, a PI3K/AKT/mTOR protein, a NCK-PAK-JNK protein, a PLC-DAG-PKC protein, or a cell cycle-associated protein kinase associated with or downstream of EGFR. In other embodiments, prevention of hearing loss is achieved by administering to a subject in need of treatment an inhibitor of a cell cycle-associated protein kinase associated with or downstream of EGFR. In certain embodiments, prevention of hearing loss is achieved by administering to a subject in need of treatment an inhibitor of Her-2, Aurora kinase, B-Raf, or PDGFR expression or activity. The inhibitor of EGFR signaling can be administered alone or in combination with one or more otoprotective agents. The term "otoprotective agent" refers to an agent that reduces or prevents noise-induced hearing loss, chemically-induced hearing loss, or age-induced hearing impairment or otherwise protects against hearing impairment. Examples of otoprotective agents include, but are not limited to, PARP-1 inhibitors; pirenzepine LS-75, otenzepad, AQ-RA741, viramune, BIBN 99, DIBD, telenzepine (see US 2011/0263574); methionine (see U.S. Pat. No. 7,071,230); IGF-1, FGF-2, aspirin, reduced glutathione, N-methyl-(D)-glucaminedithiocarbamate, and iron chelators such as tartrate and maleate. See also US 2005/0101534 for additional otoprotective agents.

Protection against and prevention or treatment of hearing loss or impairment can be in the context of conditions including, but not limited to, tinnitus, ringing, Presbyacusis, auditory neuropathy, acoustic trauma, acoustic neuroma, Pendred syndrome, Usher syndrome, Wardenburg syndrome, non-syndromic sensorineural deafness, otitis media, otosclerosis, Meniere's disease, ototoxicity, labyrinthitis, as well as hearing impairments caused by infection (i.e., measles, mumps, or meningitis), medicines such as antibiotics, and some cancer treatments (i.e., chemotherapy and radiation therapy).

In certain embodiments, the hearing impairment is drug-induced. In a still further aspect, the drug is a chemotherapeutic agent. More specifically, the drug is a platinum-based chemotherapeutic agent such as carboplatin, cisplatin, transplatin, nedaplatin, oxaliplatin, picoplatin, satraplatin, transplatin, and triplatin, or a pharmaceutically acceptable salt thereof. In a particular embodiment, the platinum-based chemotherapeutic agent is cisplatin, or a pharmaceutically acceptable salt thereof. In yet a further embodiment, the drug is an antibiotic, including, but not limited to, daunorubicin, doxorubicin, epirubicin, idarubicin, actinomycin-D, bleomycin, mitomycin-C, amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomicin, spectinomycin, streptomycin, tobramycin, and verdamicin, or a pharmaceutically acceptable salt thereof.

In a further aspect, the hearing impairment is age-related, noise-induced or a balance or orientation-related disorder. Examples of balance disorders include, but are not limited to, induced or spontaneous vertigo, dysequilibrium, increased susceptibility to motion sickness, nausea, vomiting, ataxia, labyrinthitis, oscillopsia, nystagmus, syncope, lightheadedness, dizziness, increased falling, difficulty walking at night, Meniere's disease, and difficulty in visual tracking and processing. Further, the noise-induced hearing loss may be temporary or permanent.

More than one billion teens and young adults worldwide are at risk of hearing loss from exposure to loud music, as recently reported by the World Health Organization. Many other noise exposures, including occupational settings and consumer-operated devices, also cause noise-induced hearing loss, which is among the most common physical complaints and which detracts significantly from the ability to converse, communicate, and participate in everyday life (thus reducing general quality of life of the individual and the family). Acute or chronic acoustic overexposure has put more than 40 million US workers at risk of permanent hearing loss (Kopke, et al. (2007) *Hear. Res.* 226:114-125).

Traumatic brain injury (TBI) and blast-associated injury occur most frequently in military situations where blast exposure cannot be predicted, trauma intensity exceeds the effectiveness of protective devices, or protective devices are not available. TBI is often accompanied by a diverse range of disruption or damage to the auditory sensory system, which is highly vulnerable to blast injury. Extreme physical blast force can cause damage of various types to the peripheral auditory system, including rupture of the tympanic membrane (TM, eardrum), fracture of the middle ear bones, dislocation of sensory hair cells from the basilar membrane, and loss of spiral ganglia that innervate hair cells. In human studies of blast injury, approximately 17-29% of cases involve severe TM rupture, while 33-78% involve moderate to severe sensorineural hearing loss (hair cell and ganglion loss). Therefore, TBI and blast injury are a common, although extreme, cause of hearing loss.

Biological protection of hearing is more promising than currently available mechanical protective devices. Hearing aids are frequently problematic because of their high cost and their many technical issues. Ideally, service men and women could take protective drugs before entering high-risk or high-noise settings and would then be protected from noise injury with no effect on performance. To date, there are no FDA-approved drugs for protection against noise- and TBI-associated hearing loss.

In accordance with the methods of this invention, the inhibitor of EGFR signaling can be administered locally, e.g., to the inner ear of the subject. Alternatively, the inhibitor of EGFR signaling can be administered systemically. Further, the inhibitor of EGFR signaling can be administered via injection into one or more of the scala tympani, cochlear duct, scala vestibule of the cochlea, into the auditory nerve trunk in the internal auditory meatus, or into the middle ear space across the transtympanic membrane/ear drum. Moreover, when used in combination, the EGFR signaling can be administered via the same or different routes.

In various aspects, the disclosed molecules can be used in combination with one or more other drugs in the treatment, prevention, control, amelioration, or reduction of risk of hearing impairments and disorders for which disclosed molecules or the other drugs can have utility, where the combination of the drugs together are safer or more effective than either drug alone. Such other drug(s) can be administered, by a route and in an amount commonly used therefor, contemporaneously or sequentially with a compound of the present invention. When a molecule of the present invention is used contemporaneously with one or more other drugs, a pharmaceutical composition in unit dosage form containing such other drugs and a disclosed compound is preferred. However, the combination therapy can also include therapies in which a disclosed molecule and one or more other drugs are administered on different overlapping schedules. It is also contemplated that when used in combination with one or more other active ingredients, the disclosed molecules and the other active ingredients can be used in lower doses than when each is used singly.

The methods herein are useful in the prevention or treatment of both acute and persistent, progressive disorders associated with lack of or damage to functional sensory hair cells. For acute ailments, the drugs herein can be administered using a single application or multiple applications within a short time period. For persistent diseases, such as hearing loss, or disorders stemming from a massive loss of sensory hair cells, numerous rounds of administration of the drugs herein may be necessary to realize a therapeutic effect.

Where appropriate, following treatment, the subject (e.g., human or other animal) can be tested for an improvement in hearing or in other symptoms related to hearing disorders. Subjects benefiting from treatment include those at risk of hair cell loss. For example, a subject having or at risk for developing a hearing loss can hear less well than the average subject (e.g., an average human being), or less well than a subject before experiencing the hearing loss. For example, hearing can be diminished by at least 5%, 10%, 30%, 50% or more. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain. In various aspects, treatment can be continued with or without modification or can be stopped.

Expression Vectors. One of ordinary skill in the art will appreciate that any of a number of expression vectors known in the art are suitable for introducing a nucleic acid sequence to the inner ear. Examples of suitable expression vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, AAV-adenoviral chimeric vectors, and adenovirus-based vectors. Any of these expression vectors can be prepared using standard recombinant DNA techniques described in, e.g., Sambrook, et al. (1989) *Molecular Cloning, A Laboratory Manual*, 2$^{nd}$ Ed., Cold Spring Harbor Press, Cold Spring Harbor, NY; and Ausubel, et al. (1994) *Current Protocols in Molecular Biology*, Greene Publishing Associates and John Wiley & Sons, New York, NY.

Plasmids, genetically engineered circular double-stranded DNA molecules, can be designed to contain an expression cassette for delivery of a nucleic acid sequence to the inner ear. Although plasmids were the first vector described for the administration of therapeutic nucleic acids, the level of transfection efficiency is poor compared with other techniques. By complexing the plasmid with liposomes, the efficiency of gene transfer in general is improved. While the liposomes used for plasmid-mediated gene transfer strategies have various compositions, they are typically synthetic cationic lipids. Advantages of plasmid-liposome complexes include their ability to transfer large pieces of DNA encoding a therapeutic nucleic acid and their relatively low immunogenicity. Plasmids also can be modified to prolong transgene expression as described in U.S. Pat. No. 6,165,754. Expression of a transgene in the ear using plasmids has been described (see, for example, Jero, et al. (2001) *Human Gene Ther.* 12:539-549). While plasmids are suitable for use in the inventive method, preferably the expression vector is a viral vector.

AAV vectors are viral vectors of particular interest for use in gene therapy protocols. AAV is a DNA virus, which is not known to cause human disease. AAV requires co-infection with a helper virus (i.e., an adenovirus or a herpes virus), or expression of helper genes, for efficient replication. AAV vectors used for administration of a therapeutic nucleic acid have approximately 96% of the parental genome deleted, such that only the terminal repeats (ITRs), which contain recognition signals for DNA replication and packaging, remain. This eliminates immunologic or toxic side effects due to expression of viral genes. Host cells containing an integrated AAV genome show no change in cell growth or morphology (see, for example, U.S. Pat. No. 4,797,368). Although efficient, the need for helper virus or helper genes can be an obstacle for widespread use of this vector.

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. When employing pathogenic retroviruses, e.g., human immunodeficiency virus (HIV) or human T-cell lymphotrophic viruses (HTLV), care must be taken in altering the viral genome to eliminate toxicity. A retroviral vector can additionally be manipulated to render the virus replication-incompetent. As such, retroviral vectors are thought to be particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, are particularly useful in the sensory epithelium of the inner ear where sensory cells do not regenerate.

HSV-based viral vectors are suitable for use as an expression vector to introduce nucleic acids into the inner ear for transduction of target cells. The mature HSV virion is composed of an enveloped icosahedral capsid with a viral genome composed of a linear double-stranded DNA molecule that is 152 kb. Most replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. Of course, this ability is also a disadvantage in terms of short-term treatment regimens. For a description of HSV-based vectors appropriate for use in the inventive methods, see, for example, U.S. Pat. Nos. 5,837,532, 5,846,782, 5,849,572, 5,804,413, WO 1991/02788, WO 1996/04394, WO 1998/15637, and WO 1999/06583.

Adenovirus (Ad) is a 36-kb double-stranded DNA virus that efficiently transfers DNA in vivo to a variety of different target cell types. For use in the inventive method, the virus is preferably made replication-deficient by deleting select genes required for viral replication. The expendable non-replication essential E3 region is also frequently deleted to allow additional room for a larger DNA insert. The vector can be produced in high titers and can efficiently transfer DNA to replicating and non-replicating cells. Genetic information transferred to a cell by way of an adenoviral vector remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV inverted terminal repeats (ITRs) and nucleic acid encoding the Rep protein incorporated into an adenoviral vector enables the adenoviral vector to integrate into a mammalian cell genome. Therefore, AAV-Ad chimeric vectors are an interesting option for use in the context of the invention.

Preferably, the expression vector of the inventive method is a viral vector, more preferably, the expression vector is an adenoviral vector. Adenovirus from any origin, any subtype, mixture of subtypes, or any chimeric adenovirus can be used as the source of the viral genome for the adenoviral vector of the invention. A human adenovirus preferably is used as the source of the viral genome for the replication-deficient adenoviral vector. The adenovirus can be of any subgroup or serotype. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, VA). Preferably, the adenoviral vector is of subgroup C, especially serotype 2 or even more desirably serotype 5.

However, non-group C adenoviruses, and even non-human adenoviruses, can be used to prepare replication-deficient adenoviral gene transfer vectors for delivery of DNA to target cells in the inner ear. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, 5,849,561, WO 1997/12986 and WO 1998/53087. Preferred non-human adenoviruses include, but are not limited to, simian (e.g., SAV 25), bovine, canine, porcine adenoviruses.

The adenoviral vector is preferably replication-deficient. By "replication-deficient" is meant that the adenoviral vector comprises an adenoviral genome that lacks at least one replication-essential gene function (i.e., such that the adenoviral vector does not replicate in typical host cells, especially those in the human patient that could be infected by the adenoviral vector in the course of treatment in accordance with the invention). A deficiency in a gene, gene function, or gene or genomic region, as used herein, is defined as a deletion of sufficient genetic material of the viral genome to impair or obliterate the function of the gene whose nucleic acid sequence was deleted in whole or in part. While deletion of genetic material is preferred, mutation of genetic material by addition or substitute also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2). More preferably, the replication-deficient adenoviral vector comprises an adenoviral genome deficient in at least one replication-essential gene function of one or more regions of the adenoviral genome. Preferably, the adenoviral vector is deficient in at least one gene function of the E1 region or the E4 region of the adenoviral genome required for viral replication (denoted an E1-deficient adenoviral vector or an E4-deficient adenoviral vector). In addition to a deficiency in the E1 region, the recombinant adenovirus also can have a mutation in the major late promoter (MLP), as discussed in WO 2000/00628. Most preferably, the adenoviral vector is deficient in at least one replication-essential gene function (desirably all replication-essential gene functions) of the E1 region and at least part of the nonessential E3 region (e.g., an XbaI deletion of the E3 region) (denoted an E1/E3-deficient adenoviral vector). With respect to the E1 region, the adenoviral vector can be deficient in part or all of the E1A region and part or all of the E1B region, e.g., in at least one replication-essential gene function of each of the E1A and E1B regions. When the adenoviral vector is deficient in at least one replication-essential gene function in one region of the adenoviral genome (e.g., an E1- or E1/E3-deficient adenoviral vector), the adenoviral vector is referred to as "singly replication-deficient."

The adenoviral vector of the invention can be "multiply replication-deficient," meaning that the adenoviral vector is deficient in one or more replication-essential gene functions in each of two or more regions of the adenoviral genome. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector). Ideally, the adenoviral vector lacks replication-essential gene functions of only those replication-essential gene functions encoded by the early regions of the adenoviral genome, although this is not required in all contexts of the invention. A preferred multiply deficient adenoviral vector comprises an adenoviral genome having deletions of nucleotides 457-3332 of the E1 region, nucleotides 28593-30470 of the E3 region, nucleotides 32826-35561 of the E4 region, and, optionally, nucleotides 10594-10595 of the region encoding VA-RNA1. However, other deletions may be appropriate. Nucleotides 356-3329 or 356-3510 can be removed to create a deficiency in replication essential E1 gene functions. Nucleotides 28594-30469 can be deleted from the E3 region of the adenoviral genome. While the specific nucleotide designations recited above correspond to the adenoviral serotype 5 genome, the corresponding nucleotides for non-serotype 5 adenoviral genomes can easily be determined by those of ordinary skill in the art.

The adenoviral vector, when multiply replication-deficient, especially in replication-essential gene functions of the E1 and E4 regions, preferably includes a spacer element to provide viral growth in a complementing cell line similar to that achieved by singly replication-deficient adenoviral vectors, particularly an E1-deficient adenoviral vector. The spacer element can contain any sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer element sequence can be coding or non-coding and native or non-native with respect to the adenoviral genome, but does not restore the replication-essential function to the deficient region. The use of a spacer in an adenoviral vector is described in U.S. Pat. No. 5,851,806. In one embodiment of the inventive method, the replication-deficient or conditionally replicating adenoviral vector is an E1/E4-deficient adenoviral vector wherein the L5 fiber region is retained, and a spacer is located between the L5 fiber region and the right-side ITR. More preferably, in such an adenoviral vector, the E4 polyadenylation sequence alone or, most preferably, in combination with another sequence, exists between the L5 fiber region and the right-side ITR, so as to sufficiently separate the retained L5 fiber region from the right-side ITR, such that viral production of such a vector approaches that of a singly replication-deficient adenoviral vector, particularly an E1-deficient adenoviral vector.

The adenoviral vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case it is preferred that at least either the viral ITRs and one or more promoters or the viral ITRs and a packaging signal are left intact (i.e., an adenoviral amplicon). The 5' or 3' regions of the adenoviral genome comprising ITRs and packaging sequence need not originate from the same adenoviral serotype as the remainder of the viral genome. For example, the 5' region of an adenoviral serotype 5 genome (i.e., the region of the genome 5' to the adenoviral E1 region) can be replaced with the corresponding region of an adenoviral serotype 2 genome (e.g., the Ad5 genome region 5' to the E1 region of the adenoviral genome is replaced with nucleotides 1-456 of the Ad2 genome). Suitable replication-deficient adenoviral vectors, including multiply replication-deficient adenoviral vectors, are disclosed in U.S. Pat. Nos. 5,837,511, 5,851,806, 5,994,106, US 2001/0043922, US 2002/0004040, US 2002/0031831, US 2002/0110545, WO 1995/34671, WO 1997/12986, and WO 1997/21826. Ideally, the replication-deficient adenoviral vector is present in a pharmaceutical composition virtually free of replication-competent adenovirus (RCA) contamination (e.g., the pharmaceutical composition comprises less than about 1% of RCA contamination). Most desirably, the pharmaceutical composition is RCA-free. Adenoviral vector compositions and stocks that are RCA-free are described in U.S. Pat. Nos. 5,944,106, 6,482,616, US 2002/0110545 and WO 1995/34671.

Therefore, in a preferred embodiment, the expression vector of the inventive method is a multiply replication-deficient adenoviral vector lacking all or part of the E1 region, all or part of the E3 region, all or part of the E4 region, and, optionally, all or part of the E2 region. It is believed that multiply deficient vectors are particularly suited for delivery of exogenous nucleic acid sequences to the ear. Adenoviral vectors deficient in at least one replication-essential gene function of the E1 region are most commonly used for gene transfer in vivo. However, currently used singly replication-deficient adenoviral vectors can be detrimental to the sensitive cells of the epithelium of the inner ear, causing damage to the very cells to be treated. Adenoviral vectors that are deficient in at least one replication-essential gene function of the E4 region, particularly adenoviral vectors deficient in replication-essential gene functions of the E4 region and the E1 region, are less toxic to cells than E1-deficient adenoviral vectors (see, for example, Wang, et al. (1996) *Nature Med.* 2(6):714-716 and U.S. Pat. No. 6,228,646). Accordingly, damage to existing hair cells and supporting cells can be minimized by employing an E1,E4-deficient adenoviral vector to deliver the nucleic acid sequence encoding the EGFR inhibitor to inner ear cells.

In this regard, it has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others. In view of the above, the multiply deficient adenoviral vector (e.g., the at least E4-deficient adenoviral vector) or a second expression vector comprises a nucleic acid sequence encoding a trans-acting factor that modulates the persistence of expression of the nucleic acid sequence encoding the EGFR inhibitor.

Replication-deficient adenoviral vectors are typically produced in complementing cell lines that provide gene functions not present in the replication-deficient adenoviral vectors, but required for viral propagation, at appropriate levels in order to generate high titers of viral vector stock. A preferred cell line complements for at least one and preferably all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially gene therapy purposes. The lack of RCA in the vector stock avoids the replication of the adenoviral vector in non-complementing cells. Construction of such a complementing cell lines involve standard molecular biology and cell culture techniques, such as those described by Sambrook, et al. (1989) *Molecular Cloning, a Laboratory Manual,* 2d edition, Cold Spring Harbor Press, Cold Spring Harbor, NY; and Ausubel, et al. (1994) *Current Protocols in Molecular Biology,* Greene Publishing Associates and John Wiley & Sons, New York, NY.

Complementing cell lines for producing the adenoviral vector include, but are not limited to, 293 cells (see, e.g., Graham, et al. (1977) *J. Gen. Virol.* 36:59-72), PER.C6 cells (see, e.g., WO 1997/00326, U.S. Pat. Nos. 5,994,128 and 6,033,908), and 293-ORF6 cells (see, e.g., WO 1995/34671 and Brough, et al. (1997) *J. Virol.* 71:9206-9213). In some instances, the complementing cell will not complement for all required adenoviral gene functions. Helper viruses can be employed to provide the gene functions in trans that are not encoded by the cellular or adenoviral genomes to enable replication of the adenoviral vector. Adenoviral vectors can be constructed, propagated, and/or purified using the materials and methods set forth, for example, in U.S. Pat. Nos. 5,965,358, 5,994,128, 6,033,908, 6,168,941, 6,329,200, 6,383,795, 6,440,728, 6,447,995, 6,475,757, US 2002/0034735, WO 1998/53087, WO 1998/56937, WO 1999/15686, WO 1999/54441, WO 2000/12765, WO 2001/77304, and WO 2002/29388, as well as the other references identified herein. Non-group C adenoviral vectors, including adenoviral serotype 35 vectors, can be produced using the methods set forth in, for example, U.S. Pat. Nos. 5,837,511, 5,849,561, WO 1997/12986 and WO 1998/53087. Moreover, numerous adenoviral vectors are available commercially.

The adenoviral vector's coat protein can be modified so as to decrease the adenoviral vector's ability or inability to be recognized by a neutralizing antibody directed against the wild-type coat protein. Such modifications are useful for multiple rounds of administration. Similarly, the coat protein of the adenoviral vector can be manipulated to alter the binding specificity or recognition of the adenoviral vector for a viral receptor on a potential host cell. Such manipulations can include deletion or substitution of regions of the fiber, penton, hexon, pIIIa, pVI, and/or pIX, insertions of various native or non-native ligands into portions of the coat protein, and the like. Manipulation of the coat protein can broaden the range of cells infected by the adenoviral vector or enable targeting of the adenoviral vector to a specific cell type. The ability of an adenoviral vector to recognize a potential host cell can be modulated without genetic manipulation of the coat protein, i.e., through use of a bi-specific molecule. For instance, complexing an adenovirus with a bispecific molecule comprising a penton base- or fiber-binding domain and a domain that selectively binds a particular cell surface binding site enables the targeting of the adenoviral vector to a particular cell type.

Preferably, the adenoviral capsid is modified to display a non-native amino acid sequence. The non-native amino acid sequence can be inserted into or in place of an internal coat protein sequence (e.g., within an exposed loop of an adenoviral fiber protein) or fused to the terminus of an adenoviral coat protein (e.g., fused to the C-terminus of an adenoviral fiber protein, optionally using a linker or spacer sequence). The non-native amino acid sequence can be conjugated to any of the adenoviral coat proteins to form a chimeric coat protein. Therefore, for example, the non-native amino acid sequence of the invention can be conjugated to, inserted into, or attached to a fiber protein, a penton base protein, a hexon protein, proteins IX, VI, or IIIa, etc. The sequences of such proteins, and methods for employing them in recombinant proteins, are well known in the art (see, e.g., U.S. Pat. Nos. 5,543,328, 5,559,099, 5,712,136, 5,731,190, 5,756,086, 5,770,442, 5,846,782, 5,962,311, 5,965,541, 5,846,782, 6,057,155, 6,127,525, 6,153,435, 6,329,190, 6,455,314, 6,465,253, 6,576,456, US 2001/0047081, US 2003/0099619, WO 1996/07734, WO 1996/26281, WO 1997/20051, WO 1998/07877, WO 1998/07865, WO 1998/40509, WO 1998/54346, WO 2000/15823, WO 2001/58940, and WO 2001/92549). The coat protein portion of the chimeric coat protein can be a full-length adenoviral coat protein to which the ligand domain is appended, or it can be truncated, e.g., internally or at the C- and/or N-terminus. The coat protein portion need not, itself, be native to the adenoviral vector.

Where the ligand is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber.

Preferably the ligand is added to the virion protein, and is incorporated in such a manner as to be readily exposed to the substrate (e.g., at the N- or C-terminus of the protein, attached to a residue facing the substrate, positioned on a peptide spacer to contact the substrate, etc.) to maximally present the non-native amino acid sequence to the substrate. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate. Where the non-native amino acid sequence is attached to the hexon, preferably it is within a hypervariable region (Miksza, et al. (1996) *J. Virol.* 70(3):1836-44). Use of a spacer sequence to extend the non-native amino acid sequence away from the surface of the adenoviral particle can be advantageous in that the non-native amino acid sequence can be more available for binding to a receptor and any steric interactions between the non-native amino acid sequence and the adenoviral fiber monomers is reduced.

A chimeric viral coat protein comprising a non-native ligand is desirably able to direct entry into cells of the viral, i.e., adenoviral, vector comprising the coat protein that is more efficient than entry into cells of a vector that is identical except for comprising a wild-type viral coat protein rather than the chimeric viral coat protein. Preferably, the chimeric virus coat protein binds a novel endogenous binding site present on the cell surface that is not recognized, or is poorly recognized by a vector comprising a wild-type coat protein.

In addition, the adenoviral capsid proteins can be altered to reduce or ablate binding to native adenoviral receptors (i.e., receptors bound by wild-type adenovirus). In particular, the portion of the adenoviral fiber protein which interacts with the coxsackie and adenovirus receptor (CAR) can be mutated by deletion, substitution, repositioning within the fiber protein, etc., such that the adenoviral fiber protein does not bind CAR. Likewise, the portion of the adenoviral penton protein that interacts with integrins can be altered to ablate native integrin binding. To reduce native binding and transduction of the replication-deficient or conditionally-replicating adenoviral vector, the native binding sites located on adenoviral coat proteins which mediate cell entry, e.g., the fiber and/or penton base, are absent or disrupted. Two or more of the adenoviral coat proteins are believed to mediate attachment to cell surfaces (e.g., the fiber and penton base). Any suitable technique for altering native binding to a host cell (e.g., a mesothelial cell or hepatocyte) can be employed. For example, exploiting differing fiber lengths to ablate native binding to cells can be accomplished via the addition of a binding sequence to the penton base or fiber knob. This addition can be done either directly or indirectly via a bispecific or multispecific binding sequence. Alternatively, the adenoviral fiber protein can be modified to reduce the number of amino acids in the fiber shaft, thereby creating a "short-shafted" fiber (as described in, for example, U.S. Pat. No. 5,962,311). The fiber proteins of some adenoviral serotypes are naturally shorter than others, and these fiber proteins can be used in place of the native fiber protein to reduce native binding of the adenovirus to its native receptor. For example, the native fiber protein of an adenoviral vector derived from serotype 5 adenovirus can be switched with the fiber protein from adenovirus serotypes 40 or 41.

In this regard, the adenoviral vector can be modified to include an adenoviral coat protein (e.g., fiber, penton, or hexon protein) from a different serotype of adenovirus. For example, an adenoviral serotype 5 adenovirus can be modified to display an adenovirus serotype 35 fiber, which, in turn, can optionally comprise one or more non-native amino acid ligands. It is possible to utilize an adenoviral vector which does not naturally infect cell types of the inner ear to target the vector to a particular cell type. Alternatively, an adenoviral vector which naturally transduces cells of the inner ear can be modified to display an adenoviral fiber protein and/or adenoviral penton base derived from an adenovirus which has no natural tropism for target cells, which adenoviral vector can display a non-native amino acid sequence that enables transduction of target cells.

In another embodiment, the nucleic acid residues associated with native substrate binding can be mutated (see, e.g., WO 2000/15823; Einfeld, et al. (2001) *J. Virol.* 75(23): 11284-11291; van Beusechem, et al. (2002) *J. Virol.* 76(6): 2753-2762) such that the adenoviral vector incorporating the mutated nucleic acid residues is less able to bind its native substrate. For example, adenovirus serotypes 2 and 5 transduce cells via binding of the adenoviral fiber protein to the coxsackievirus and adenovirus receptor (CAR) and binding of penton proteins to integrins located on the cell surface. Accordingly, the replication-deficient or conditionally-replicating adenoviral vector of the inventive method can lack native binding to CAR and/or exhibit reduced native binding to integrins. To reduce native binding of the replication-deficient or conditionally-replicating adenoviral vector to host cells, the native CAR and/or integrin binding sites (e.g., the RGD sequence located in the adenoviral penton base) are removed or disrupted.

Modifications to adenoviral coat proteins can enhance the resulting adenoviral vectors' ability to evade the host immune system. In one embodiment, the adenoviral vector is selectively targeted to scarred epithelial cells (e.g., regions of the epithelium missing endogenous, functional hair cells) by ablation of native binding of the adenoviral vector to CAR and/or integrins and incorporation into the adenoviral capsid one or more non-native ligands. Suitable ligands that mediate transduction via a specific receptor can be determined using routine library display techniques (such as phage display) and include, for example, ligands bound by EGF and ligands from the FGF family of peptides. Other examples of non-native amino acid sequences and their substrates include, but are not limited to, short (e.g., 6 amino acids or less) linear stretches of amino acids recognized by integrins, as well as polyamino acid sequences such as polylysine, polyarginine, etc. Non-native amino acid sequences for generating chimeric adenoviral coat proteins are further described in U.S. Pat. No. 6,455,314 and WO 2001/92549.

Suitable modifications to an adenoviral vector are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, 6,465,253, US 2001/0047081, US 2002/0099024, US 2002/0151027, WO 1996/07734, WO 1996/26281, WO 1997/20051, WO 1998/07865, WO 1998/07877, WO 1998/40509, WO 1998/54346, WO 2000/15823, WO 2001/58940, and WO 2001/92549. The construction of adenoviral vectors is well understood in the art. Adenoviral vectors can be constructed and/or purified using the methods set forth, for example, in U.S. Pat. Nos. 5,965,358, 6,168,941, 6,329,200, 6,383,795, 6,440,728, 6,447,995, 6,475,757, WO 1998/53087, WO 1998/56937, WO 1999/15686, WO 1999/54441, WO 2000/12765, WO 2001/77304, and WO 2002/29388, as well as the other references identified herein. Moreover, numerous expression vectors, including adenoviral vectors, are available commercially. Adeno-associated viral vectors can be constructed and/or purified using the methods set forth, for example, in U.S. Pat. No. 4,797,368 and Laughlin, et al. (1983) *Gene* 23:65-73.

The selection of an expression vector for use in the inventive method depends on a variety of factors such as, for example, the host, immunogenicity of the vector, the desired duration of protein production, the target cell, and the like. As each type of expression vector has distinct properties, the inventive method can be tailored to any particular situation. Moreover, more than one type of expression vector can be used to deliver the nucleic acid sequence to the target cell. Thus, the invention provides method of changing the sensory perception and preventing or treating hearing loss in an animal, wherein the method comprises administering to the inner ear at least two different expression vectors comprising a nucleic acid sequence encoding an inhibitor of EGFR signaling. Preferably, the target cell in the inner ear, e.g., a supporting cell, is contacted with an adenoviral vector and an HSV vector, in that adenoviral vectors efficiently transduce supporting cells and HSV vectors efficiently transduce neurons. One of ordinary skill in the art will appreciate the ability to capitalize on the advantageous properties of multiple delivery systems to treat or study sensory disorders of the inner ear.

Nucleic Acid Molecules. The expression vector of this invention harbors nucleic acid molecules. Ideally, the nucleic acid molecules encode an inhibitor of EGFR signaling. One of ordinary skill in the art will appreciate that any transcription factor, e.g., inhibitor of EGFR signaling, can be modified or truncated and retain activity. As such, therapeutic fragments (i.e., those fragments having biological activity sufficient to, for example, activate transcription) also are suitable for incorporation into the expression vector. Likewise, a fusion protein composed of a transcription factor or a therapeutic fragment thereof and, for example, a moiety that stabilizes peptide conformation, also can be present in the expression vector.

Nucleic acid molecules (i.e., encoding an inhibitor of EGFR signaling) are desirably present as part of an expression cassette, i.e., a particular base sequence that possesses functions which facilitate subcloning and recovery of a nucleic acid molecule (e.g., one or more restriction sites) or expression of a nucleic acid molecule (e.g., polyadenylation or splice sites). When the expression cassette is an adenoviral vector, the nucleic acid molecule of interest (e.g., encoding an inhibitor of EGFR signaling) can be located in the E1 region (e.g., replaces the E1 region in whole or in part) or can be located in the E4 region of the adenoviral genome. When positioned in the E4 region, a spacer sequence is not required. The expression cassette is preferably inserted in a 3'→5' orientation, e.g., oriented such that the direction of transcription of the expression cassette is opposite that of the surrounding adenoviral genome. While a single expression cassette can be inserted into an adenoviral vector for expressing an inhibitor of EGFR signaling, in other embodiments, the adenoviral vector can include multiple expression cassettes harboring nucleic acid molecules encoding an inhibitor of EGFR signaling, wherein said cassettes can replace any of the deleted regions of the adenoviral genome. The insertion of an expression cassette into the adenoviral genome (e.g., the E1 region of the genome) can be facilitated by known methods, for example, by the introduction of a unique restriction site at a given position of the adenoviral genome. As set forth above, preferably the E3 region of the adenoviral vector is deleted, and the E4 region is replaced by a spacer element.

For expression, the nucleic acid molecule of interest is operably linked to regulatory sequences necessary for said expression, e.g., a promoter. A "promoter" is a DNA sequence that directs the binding of RNA polymerase and thereby promotes RNA synthesis. A nucleic acid molecule is "operably linked" to a promoter when the promoter is capable of directing transcription of that nucleic acid molecule. A promoter can be native or non-native to the nucleic acid molecule to which it is operably linked. Any promoter (i.e., whether isolated from nature or produced by recombinant DNA or synthetic techniques) can be used in connection with the invention to provide for transcription of the nucleic acid molecule. The promoter preferably is capable of directing transcription in a eukaryotic (desirably mammalian) cell. The functioning of the promoter can be altered by the presence of one or more enhancers (e.g., the CMV immediate early enhancer) and/or silencers.

The invention preferentially employs a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner, et al. (1981) *Proc. Natl. Acad. Sci. USA* 78:144-145), promoters derived from SV40 or Epstein Barr virus, an adeno-associated viral promoter, such as the p5 promoter, and the like. Preferably, the viral promoter is an adenoviral promoter, such as the Ad2 or Ad5 major late promoter and tripartite leader, a CMV promoter (murine or human in origin), or an RSV promoter.

The promoter need not be a viral promoter. For example, the promoter can be a cellular promoter, i.e., a promoter that drives expression of a cellular protein. Preferred cellular promoters for use in the invention will depend on the desired expression profile to produce the therapeutic agent(s). In one aspect, the cellular promoter is preferably a constitutive promoter that works in a variety of cell types. Suitable constitutive promoters can drive expression of genes encoding transcription factors, housekeeping genes, or structural genes common to eukaryotic cells. For example, the Ying Yang 1 (YY1) transcription factor (also referred to as NMP-1, NF-E1, and UCRBP) is a ubiquitous nuclear transcription factor that is an intrinsic component of the nuclear matrix (Guo, et al. (1995) *Proc. Natl. Acad. Sci. USA* 92:10526-10530). JEM-1 (also known as HGMW and BLZF-1; Tong, et al. (1998) *Leukemia* 12(11):1733-1740; Tong, et al. (2000) *Genomics* 69(3):380-390), a ubiquitin promoter, specifically UbC (Marinovic, et al. (2002) *J. Biol. Chem.* 277(19):16673-16681), a β-actin promoter, such as that derived from chicken, and the like are appropriate for use in the inventive method.

Many of the above-described promoters are constitutive promoters. Instead of being a constitutive promoter, the promoter can be an inducible promoter, i.e., a promoter that is up- and/or down-regulated in response to appropriate signals. For instance, suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed. The promoter sequence that regulates expression of the nucleic acid molecule can contain at least one heterologous regulatory sequence responsive to regulation by an exogenous agent. The regulatory sequences are preferably responsive to exogenous agents such as, but not limited to, drugs, hormones, or other gene products. For example, the regulatory sequences, e.g., promoter, preferably are responsive to glucocorticoid receptor-hormone complexes, which, in turn, enhance the level of transcription of a therapeutic peptide or a therapeutic fragment thereof.

Preferably, the promoter is a tissue-specific promoter, i.e., a promoter that is preferentially activated in a given tissue and results in expression of a gene product in the tissue where activated. A tissue specific promoter for use in this invention can be chosen by the ordinarily skilled artisan based upon the target tissue or cell-type. Suitable promoters include, but are not limited to, BRN.3C, BRN 3.1, the POU ORFS factor promoter, BRK1, BRK3, the chordin promoter, the noggin promoter, the jagged1 promoter, the jagged2 promoter, and the notch1 promoter. Preferred tissue-specific promoters for use in this invention are specific to supporting cells or sensory hair cells, such as a myosin VIIa promoter, which function in hair cells, or a hes-1 promoter, which functions in supporting cells. Ideally, a promoter is selected that promotes transgene expression in scarred epithelium.

A promoter also can be selected for use in this invention by matching its particular pattern of activity with the desired pattern and level of expression of the desired protein. Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity is especially preferred for use in many embodiments of the inventive method. It is also possible to select a promoter with an expression profile that can be manipulated by an investigator.

Along these lines, to optimize protein production, preferably the nucleic acid molecule further includes a polyadenylation site following the coding region of the nucleic acid molecule. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence. Also, preferably all the proper transcription signals (and translation signals, where appropriate) are correctly arranged such that the nucleic acid molecule is properly expressed in the cells into which it is introduced. If desired, the nucleic acid molecule also can incorporate splice sites (i.e., splice acceptor and splice donor sites) to facilitate mRNA production. Moreover, if the nucleic acid molecule encodes a protein or peptide, which is a processed or secreted protein or acts intracellularly, preferably the nucleic acid molecule further includes the appropriate sequences for processing, secretion, intracellular localization, and the like.

In certain embodiments, it may be advantageous to modulate expression of the inhibitor of EGFR signaling. An especially, preferred method of modulating expression of a nucleic acid molecule involves the addition of site-specific recombination sites on the expression vector. Contacting an expression vector having site-specific recombination sites with a recombinase will either up- or down-regulate transcription of a coding sequence, or simultaneously up-regulate transcription of one coding sequence and down-regulate transcription of another, through the recombination event.

Use of site-specific recombination to modulate transcription of a nucleic acid sequence is described in, for example, U.S. Pat. Nos. 5,801,030, 6,063,627 and WO 97/09439.

Several options are available for delivering nucleic acid molecules encoding the inhibitor of EGFR signaling to the inner ear. The multiple coding sequences can be operably linked to different promoters, e.g., different promoters having dissimilar levels and patterns of activity. Alternatively, the multiple coding sequences can be operably linked to the same promoter to form a polycistronic element. The invention also contemplates administering to the inner ear a cocktail of expression vectors, wherein each expression vectors encode an inhibitor of EGFR signaling. The cocktail of expression vectors can further include different types of expression vectors, e.g., adenoviral vectors and adeno-associated viral vectors.

In view of the above, the invention further provides an adenoviral vector harboring a nucleic acid molecule(s) encoding an inhibitor of EGFR signaling, wherein the nucleic acid molecule(s) is operably linked to regulatory sequences necessary for expression of the inhibitor of EGFR signaling. The adenoviral vector is deficient in at least one replication-essential gene function of at least the E4 region. The nucleic acid molecule can be obtained from any source, e.g., isolated from nature, synthetically generated, isolated from a genetically engineered organism, and the like. Appropriate adenoviral vectors and regulatory sequences are discussed herein.

Moreover, the invention further provides a method of generating a hair cell in differentiated sensory epithelia in vivo. The method involves contacting differentiated sensory epithelial cells with an adenoviral vector (a) deficient in one or more replication-essential gene functions of the E1 region, the E4 region, and, optionally, one or more gene functions the E3 region, (b) having a spacer in the E4 region, and (c) harboring a nucleic acid molecule(s) encoding an inhibitor of EGFR signaling. The nucleic acid molecule(s) is expressed to produce the inhibitor of EGFR signaling.

Routes of Administration. One skilled in the art will appreciate that suitable methods of administering a drug or an expression vector, such as an adenoviral vector, to the inner ear are available. Although more than one route can be used to administer a particular drug or expression vector, a particular route can provide a more immediate and more effective reaction than another route. Accordingly, the described routes of administration are merely exemplary and are in no way limiting.

No matter the route of administration, a drug or expression vector of the inventive method ideally reaches the sensory epithelium of the inner ear. The most direct routes of administration, therefore, entail surgical procedures which allow access to the interior of the structures of the inner ear. Inoculation via cochleostomy allows administration of an expression vector directly to the regions of the inner ear associated with hearing. Cochleostomy involves drilling a hole through the cochlear wall, e.g., in the otic capsule below the stapedial artery as described in Kawamoto, et al. ((2001) *Molecular Therapy* 4(6):575-585), and release of a pharmaceutical composition containing the drug or expression vector. Administration to the endolymphatic compartment is particularly useful for administering an adenoviral vector to the areas of the inner ear responsible for hearing. Alternatively, a drug or expression vector can be administered to the semicircular canals via canalostomy. Canalostomy provides for transgene expression in the vestibular system and the cochlea, whereas cochleostomy does not provide as efficient transduction in the vestibular space. The risk of damage to cochlear function is reduced using canalostomy in as much as direct injection into the cochlear space can result in mechanical damage to hair cells (Kawamoto, et al., supra). Administration procedures also can be performed under fluid (e.g., artificial perilymph), which can include factors to alleviate side effects of treatment or the administration procedure, such as apoptosis inhibitors or anti-inflammatories.

Another direct route of administration to the inner ear is through the round window, either by injection or topical application to the round window. Administration via the round window is especially preferred for delivering a drug or adenoviral vector to the perilymphatic space. Transgene expression in cochlear and vestibular neurons and cochlear sensory epithelia has been observed following administration of expression vectors via the round window (Staecker, et al. (2001) *Acta Otolaryngol.* 121:157-163). Of note, it appears possible that uptake of expression vectors, in particular non-targeted adenoviral vectors, into cells of the inner ear is not receptor-mediated. In other words, it does not appear that adenoviral infection of cells of the inner ear is mediated by CAR or integrins. To increase transduction of cells in the Organ of Corti following administration to the perilymphatic compartment, an adenoviral vector can display one or more ligands that enhance uptake of the adenoviral vector into target cells (e.g., supporting cells, cells of the stria vascularis, etc.). In this regard, the adenoviral vector can encode one or more adenoviral coat proteins which are modified to reduce native binding (e.g., CAR- and/or integrin-binding) and harbor a non-native amino acid sequence which enhances uptake of the adenoviral vector by target cells of the inner ear.

A drug or expression vector (e.g., adenoviral vector) can be present in a pharmaceutical composition for administration to the inner ear. In certain cases, it may be appropriate to administer multiple applications and/or employ multiple routes, e.g., canalostomy and cochleostomy, to ensure sufficient exposure of supporting cells to the drug or expression vector.

A drug or expression vector can be present in or on a device that allows controlled or sustained release of the drug or expression vector, such as a sponge, meshwork, mechanical reservoir or pump, or mechanical implant. For example, a biocompatible sponge or gelform soaked in a pharmaceutical composition containing the drug or expression vector is placed adjacent to the round window, through which the drug or expression vector permeates to reach the cochlea (as described in Jero, et al., supra). Mini-osmotic pumps provide sustained release of a drug or expression vector over extended periods of time (e.g., five to seven days), allowing small volumes of composition containing the drug or expression vector to be administered, which can prevent mechanical damage to endogenous sensory cells. The drug or expression vector also can be administered in the form of sustained-release formulations (see, e.g., U.S. Pat. No. 5,378,475) containing, for example, gelatin, chondroitin sulfate, a polyphosphoester, such as bis-2-hydroxyethyl-terephthalate (BHET), or a polylactic-glycolic acid.

Alternatively, the drug or expression vector can be administered parenterally, intramuscularly, intravenously, orally or intraperitoneally. As discussed herein, an expression vector can be modified to alter the binding specificity or recognition of an expression vector for a receptor on a potential host cell. With respect to adenovirus, such manipulations can include deletion of regions of the fiber, penton, or hexon, insertions of various native or non-native ligands into portions of the coat protein, and the like. One of ordinary skill in the art will appreciate that parenteral administration can require large doses or multiple administrations to effectively deliver the expression vector to the appropriate host cells. Pharmaceutically acceptable carriers for compositions are well-known to those of ordinary skill in the art (see *Pharmaceutics and Pharmacy Practice*, (1982) J. B. Lippincott Co., Philadelphia, PA, Banker and Chalmers, eds., pages 238-250; *ASHP Handbook on Injectable Drugs* (1986) Toissel, $4^{th}$ ed., pages 622-630). Although less preferred, the expression vector can also be administered in vivo by particle bombardment, i.e., a gene gun.

One of ordinary skill in the art also will appreciate that dosage and routes of administration can be selected to minimize loss of expression vector due to a host's immune system. For example, for contacting target cells in vivo, it can be advantageous to administer to a host a null expression vector (i.e., an expression vector not harboring the nucleic acid molecule(s) of interest) prior to performing the inventive method. Prior administration of null expression vectors can serve to create an immunity in the host to the expression vector hinder the body's innate clearance mechanisms, thereby decreasing the amount of vector cleared by the immune system.

Dosage. The dose of a drug or expression vector administered to an animal, particularly a human, in accordance with the invention should be sufficient to affect the desired response in the animal over a reasonable time frame. One skilled in the art will recognize that dosage will depend upon a variety of factors, including the age, species, location of damaged sensory epithelia, the pathology in question (if any), and condition or disease state. Dosage also depends on the inhibitor of EGFR signaling and/or cell cycle-associated protein kinase inhibitor, as well as the amount of sensory epithelium to be transduced. The size of the dose also will be determined by the route, timing, and frequency of administration as well as the existence, nature, and extent of any adverse side effects that might accompany the administration of a particular expression vector (e.g., surgical trauma) or drug and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. When the expression vector is a viral vector, most preferably an adenoviral vector, about $10^5$ viral particles to about $10^{12}$ viral particles are delivered to the patient. In other words, a pharmaceutical composition can be administered that includes an expression vector concentration of about $10^8$ particles/ml to about $10^{13}$ particles/ml (including all integers within the range of about $10^8$ particles/ml to about $10^{13}$ particles/ml), preferably about $10^{10}$ particles/ml to about $10^{12}$ particles/ml, and will typically involve the administration of about 0.1 µl to about 100 µl of such a pharmaceutical composition directly to the inner ear. In view of the above, the dose of one administration preferably is at least about $1\times10^6$ particles (e.g., about $4\times10^6$-$4\times10^{12}$ particles), more preferably at least about $\times10^7$ particles, more preferably at least about $1\times10^8$ particles (e.g., about $4\times10^8$-$4\times10^{11}$ particles), and most preferably at least about $1\times10^9$ particles to at least about $1\times10^{10}$ particles (e.g., about $4\times10^9$-$4\times10^{10}$ particles) of an adenoviral vector harboring a nucleic acid molecule encoding an EGFR inhibitor and/or a co- factor and/or inhibitor of a gene silencing complex. Alternatively, the dose of the pharmaceutical composition includes no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ particles). In other words, a single dose of pharmaceutical composition can be about $1\times10^6$ particle units (pu), $4\times10^6$ pu, $1\times10^7$ pu, $4\times10^7$ pu, $1\times10^8$ pu, $4\times10^8$ pu, $1\times10^9$ pu, $4\times10^9$ pu, $1\times10^{10}$ pu, $4\times10^{10}$ pu, $1\times10^{11}$ pu, $4\times10^{11}$ pu, $1\times10^{11}$ pu, $4\times10^{11}$ pu, $1\times10^{12}$ pu, or $4\times10^{12}$ pu of the adenoviral vector (e.g., the replication-deficient adenoviral vector). When the expression vector is a plasmid, preferably about 0.5 ng to about 1000 µg of DNA is administered. More preferably, about 0.1 µg to about 500 µg is administered, even more preferably about 1 µg to about 100 µg of DNA is administered. Most preferably, about 50 µg of DNA is administered to the inner ear. Of course, other routes of administration may require smaller or larger doses to achieve a therapeutic effect. Any necessary variations in dosages and routes of administration can be determined by the ordinarily skilled artisan using routine techniques known in the art.

The interior space of the structures of the inner ear is limited. The volume of pharmaceutical composition administered directly into the inner ear structures should be carefully monitored, as forcing too much composition will damage the sensory epithelium. For a human patient, the volume administered is preferably about 10 µl to about 2 ml (e.g., from about 25 µl to about 1.5 ml) of composition. For example, from about 50 pl to about 1 ml (e.g., about 100 µl, 200 µl, 300 µl, 400 µl, 500 µl, 600 µl, 700 µl, 800 µl or 900 µl) of composition can be administered. In one embodiment, the entire fluid contents of the inner ear structure, e.g., the cochlea or semi-circular canals, is replaced with pharmaceutical composition. In another embodiment, a pharmaceutical composition of the invention is slowly released into the inner ear structure, such that mechanical trauma is minimized.

It can be advantageous to administer two or more (i.e., multiple) doses of the drug or expression vector harboring a nucleic acid molecule encoding an inhibitor of EGFR signaling. The inventive method provides for administration of multiple doses of a drug or expression vector to change the sensory perception of an animal. For example, at least two doses of a drug or expression vector can be administered to the same ear. Preferably, the multiple doses are administered while retaining gene expression above background levels. Also preferably, the sensory epithelium of the inner ear is contacted with two doses or more of the drug or expression vector within about 30 days. More preferably, two or more applications are administered to the inner ear within about 90 days. However, three, four, five, six, or more doses can be administered in any time frame (e.g., 2, 7, 10, 14, 21, 28, 35, 42, 49, 56, 63, 70, 77, 85 or more days between doses).

Pharmaceutical Composition. A drug or expression vector of the invention desirably is administered in a pharmaceutical composition, which includes a pharmaceutically acceptable carrier and the drug or expression vector(s). Any suitable pharmaceutically acceptable carrier can be used within the context of the invention, and such carriers are well known in the art. The choice of carrier will be determined, in part, by the particular site to which the composition is to be administered and the particular method used to administer the composition. Ideally, in the context of adenoviral vectors, the pharmaceutical composition preferably is free of replication-competent adenovirus.

Suitable formulations include aqueous and non-aqueous solutions, isotonic sterile solutions, which can contain antioxidants, buffers, bacteriostats, and solutes that render the formulation isotonic with the blood or fluid of the inner ear of the intended recipient, and aqueous and non-aqueous sterile suspensions that can include suspending agents, solubilizers, thickening agents, stabilizers, and preservatives. The formulation can include artificial endolymph or perilymph, which are commercially available. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the pharmaceutically acceptable carrier is a buffered saline solution. More preferably, the expression vector for use in the inventive method is administered in a pharmaceutical composition formulated to protect the expression vector from damage prior to administration. For example, the pharmaceutical composition can be formulated to reduce loss of the expression vector on devices used to prepare, store, or administer the expression vector, such as glassware, syringes, or needles. The pharmaceutical composition can be formulated to decrease the light sensitivity and/or temperature sensitivity of the expression vector. To this end, the pharmaceutical composition preferably includes a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a pharmaceutical composition will extend the shelf-life of the vector, facilitate administration, and increase the efficiency of the inventive method. In this regard, a pharmaceutical composition also can be formulated to enhance transduction efficiency. In addition, one of ordinary skill in the art will appreciate that the expression vector, e.g., viral vector, can be present in a composition with other therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the viral vector. Immune system suppressors can be administered in combination with the inventive method to reduce any immune response to the vector itself or associated with a disorder of the inner ear. Angiogenic factors, neurotrophic factors, proliferating agents, and the like can be present in the pharmaceutical composition. Similarly, vitamins and minerals, anti-oxidants, and micronutrients can be co-administered. Antibiotics, i.e., microbicides and fungicides, can be present to reduce the risk of infection associated with gene transfer procedures and other disorders.

As discussed herein, several options are available for delivering multiple coding sequences to the inner ear. The nucleic acid molecule(s) encoding the inhibitor of EGFR signaling can encode additional gene products. The expression vector alternatively, or in addition, can include multiple expression cassettes encoding different gene products. Multiple coding sequences can be operably linked to different promoters, e.g., different promoters having dissimilar levels and patterns of activity. Alternatively, the multiple coding sequences can be operably linked to the same promoter to form a polycistronic element. The invention also contemplates administering to the inner ear a cocktail of expression vectors, wherein each expression vector encodes a gene product beneficial to sensory perception. The cocktail of expression vectors can further comprise different types of expression vectors, e.g., adenoviral vectors and adeno-associated viral vectors.

Alternatively, or in addition to the administration of an inhibitor of EGFR signaling, the inventive method also includes the administration of an expression vector harboring a nucleic acid molecule encoding an inhibitor of EGFR signaling, which is not encoded by an expression vector. In this respect, the method and pharmaceutical compositions disclosed herein can be modified to include the expression vector harboring a nucleic acid molecule encoding a factor in combination with an isolated inhibitory RNA molecule, protein, peptide, antibody, or small organic molecule that inhibits EGFR signaling. Moreover, the method and pharmaceutical compositions disclosed herein can be modified to include (i) the expression vector(s) harboring a nucleic acid molecule(s) encoding an inhibitor of EGFR signaling in combination with (ii) an isolated inhibitory RNA molecule, protein, peptide, antibody, or small organic molecule that inhibits EGFR signaling.

For carrying out the methods disclosed herein, this invention also provides a kit. Ideally, the kit includes a nucleic acid molecule encoding an EGFR inhibitor, and (i) a nucleic acid molecule encoding an inhibitor of epidermal growth factor receptor (EGFR) signaling; (ii) an isolated inhibitor of EGFR signaling (e.g., an inhibitory RNA or small organic molecule that inhibits one or more of EGFR, Ras, Raf, MEK, ERK/MAPK, JAK, STAT, PI3K, AKT, mTOR, NCK, PAK, JNK, PLC, PKC or a cell cycle associated kinase); or (iii) a combination of (i) and (ii). In addition, the kit can include containers (e.g., vials, bottles, syringes, or tubes) containing the active ingredients in lyophilized or liquid form as well as instructions for using the kit components including information regarding dosing, administration, timing of administration and the like. The kit may further include an indication of the active ingredients, reference to scientific literature, packing materials, clinical trial results, and the like. The information may be based on the results of various studies, for example, studies using experimental animals involving in vivo models and studies based on human clinical trials.

In one preferred embodiment, the inventive method also contemplates delivery of a nucleic acid molecule encoding at least one neurotrophic agent. Ideally, the neurotrophic agent is a neural growth stimulator, which induces growth, development, and/or maturation of neural processes. Neurotrophic factors also can be administered to protect or maintain existing and developing neurons. For a newly generated hair cell to function properly, a neural network should be in place to transmit neural impulses to the brain. Accordingly, it is advantageous to protect existing neurons associated with the sensory epithelium of the inner ear, induce the growth and maturation of new neural processes, and/or simply direct existing neural processes to sensory hair cells. Neurotrophic factors are divided into three subclasses: neuropoietic cytokines; neurotrophins; and the fibroblast growth factors. Ciliary neurotrophic factor (CNTF) is exemplary of neuropoietic cytokines. CNTF promotes the survival of ciliary ganglionic neurons and supports certain neurons that are NGF-responsive. Neurotrophins include, for example, brain-derived neurotrophic factor (BDNF) and nerve growth factor (NGF), which stimulates neurite outgrowth. Other neurotrophic factors include, for example, transforming growth factors, glial cell-line derived neurotrophic factor (GDNF), neurotrophin 3, neurotrophin 4/5, and interleukin 1-β. Neuronotrophic factors enhance neuronal survival and also are suitable for use in the inventive method. It has been postulated that neuronotrophic factors can actually reverse degradation of neurons. Such factors, conceivably, are useful in treating the degeneration of neurons associated with age, infection, or trauma. A preferred neuronotrophic factor is pigment epithelium derived factor (PEDF). PEDF is further described in Chader (1987) *Cell Different.* 20:209-216; Pignolo, et al. (1998) *J. Biol. Chem.* 268(12):8949-8957; U.S. Pat. No. 5,840,686, WO 1993/24529, WO 1999/04806, and WO 2001/58494.

The method of the invention can be part of a treatment regimen involving other therapeutic modalities. It is appropriate, therefore, if the inventive method is employed to prophylactically or therapeutically treat a sensory disorder, namely a hearing disorder or a balance disorder, that has been treated, is being treated, or will be treated with any of a number of other therapies, such as drug therapy or surgery. The inventive method also can be performed in conjunction with the implantation of hearing devices, such as cochlear implants. The inventive method also is particularly suited for procedures involving stem cells to regenerate populations of cells within the inner ear. In this respect, the inventive method can be practiced ex vivo to transduce stem cells, which are then implanted within the inner ear.

The expression vector is preferably administered as soon as possible after it has been determined that an animal, such as a mammal, specifically a human, is at risk for degeneration of sensory hair cells (prophylactic treatment) or has demonstrated reduced numbers or damage of sensory hair cells (therapeutic treatment). Treatment will depend, in part, upon the particular nucleic acid molecule used, the particular inhibitor of EGFR signaling expressed, the expression vector, the route of administration, and the cause and extent, if any, of hair cell loss or damage realized.

An expression vector(s) harboring a nucleic acid molecule (s) encoding an inhibitor of EGFR signaling can be introduced ex vivo into cells previously removed from a given animal, in particular a human. Such transduced autologous or homologous host cells can be progenitor cells that are reintroduced into the inner ear of the animal or human to express the inhibitor of EGFR signaling and maintain mature hair cells in vivo. One of ordinary skill in the art will understand that such cells need not be isolated from the patient, but can instead be isolated from another individual and implanted into the patient.

The inventive method also can involve the co-administration of other pharmaceutically active compounds. By "co-administration" is meant administration before, concurrently with, e.g., in combination with the expression vector in the same formulation or in separate formulations, or after administration of the expression vector as described above. For example, factors that control inflammation, such as ibuprofen or steroids, can be co-administered to reduce swelling and inflammation associated with administration of the expression vector. Immunosuppressive agents can be co-administered to reduce inappropriate immune responses related to an inner ear disorder or the practice of the inventive method. Similarly, vitamins and minerals, antioxidants, and micronutrients can be co-administered. Antibiotics, i.e., microbicides and fungicides, can be co-administered to reduce the risk of infection associated with surgical procedures.

The following non-limiting examples are provided to further illustrate the present invention.

Example 1: EGFR Inhibitors for Protection Against Hearing Loss

A screen of a library composed of 75 kinase inhibitors was conducted to identify inhibitors that protect against cisplatin-induced hair cell loss. This screen identified four compounds: (1) Her2 inhibitor MUBRITINIB (TAK 165), (2) Pan-AUR inhibitor SNS314 (3) BRAF-V600E inhibitor GSK2118436A (DABRAFENIB), and (4) PDGFR inhibitor CRENOLANIB that potently protected against cisplatin-induced cell death in a mouse cochlea-derived cell line (HEI-OC1) as well as cisplatin-induced hair cell loss in mouse cochlear explants.

Figure 1:
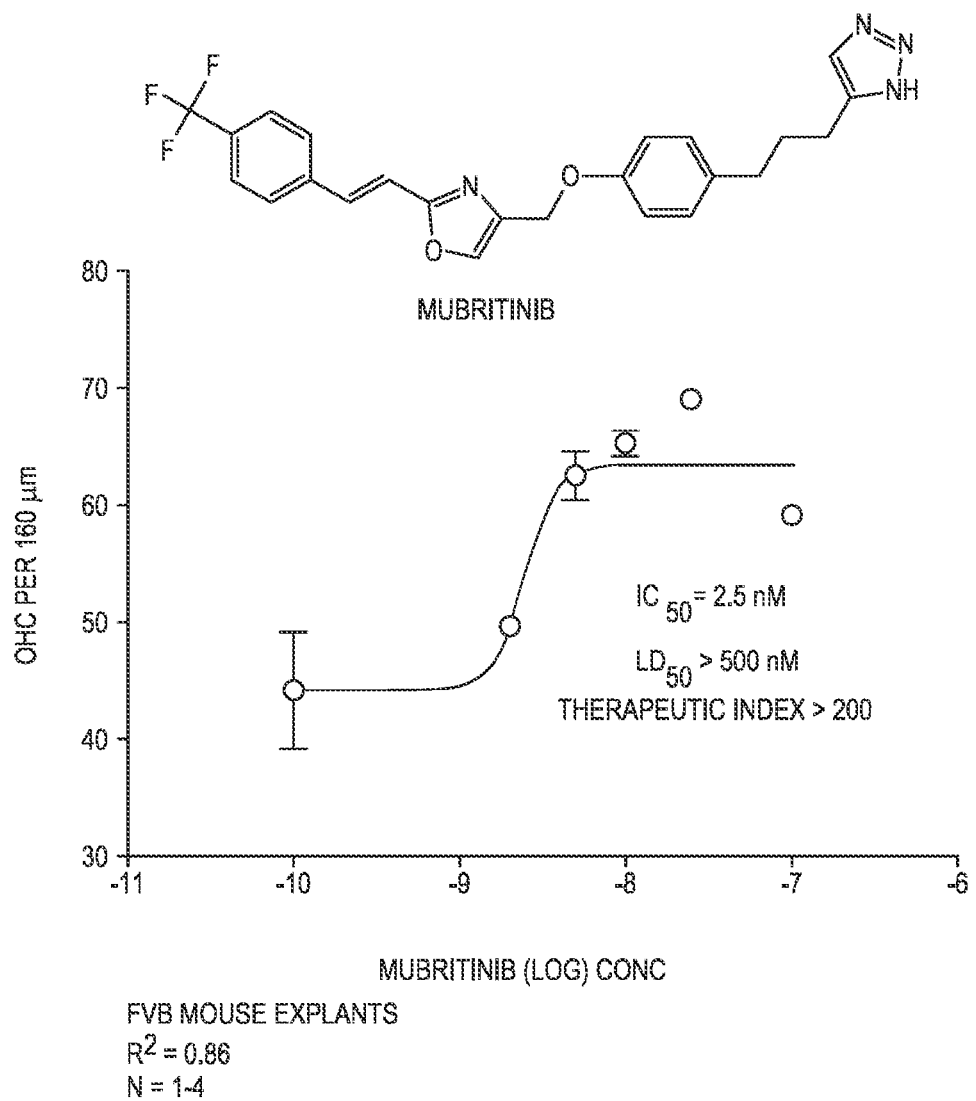
FIG. 1 shows that the EGFR inhibitor MUBRITINIB (whose structure is shown) protects against cisplatin-induced hair cell loss in mouse cochlear explants with $IC_{50}$ of 2.5 nM and $LD_{50}$ of >500 nM (Therapeutic Index of >200). Number of explants: 1-4 at each dose; FVB mouse cochlear explants were treated with 150 µM cisplatin and cochlear middle turns were analyzed; curve fitting with $R^2$ of 0.86. Note that $IC_{50}$ values of MUBRITINIB were consistent in all assays (HEI-OC1 cells and explants) demonstrating its specificity and potency.
Figure 2:
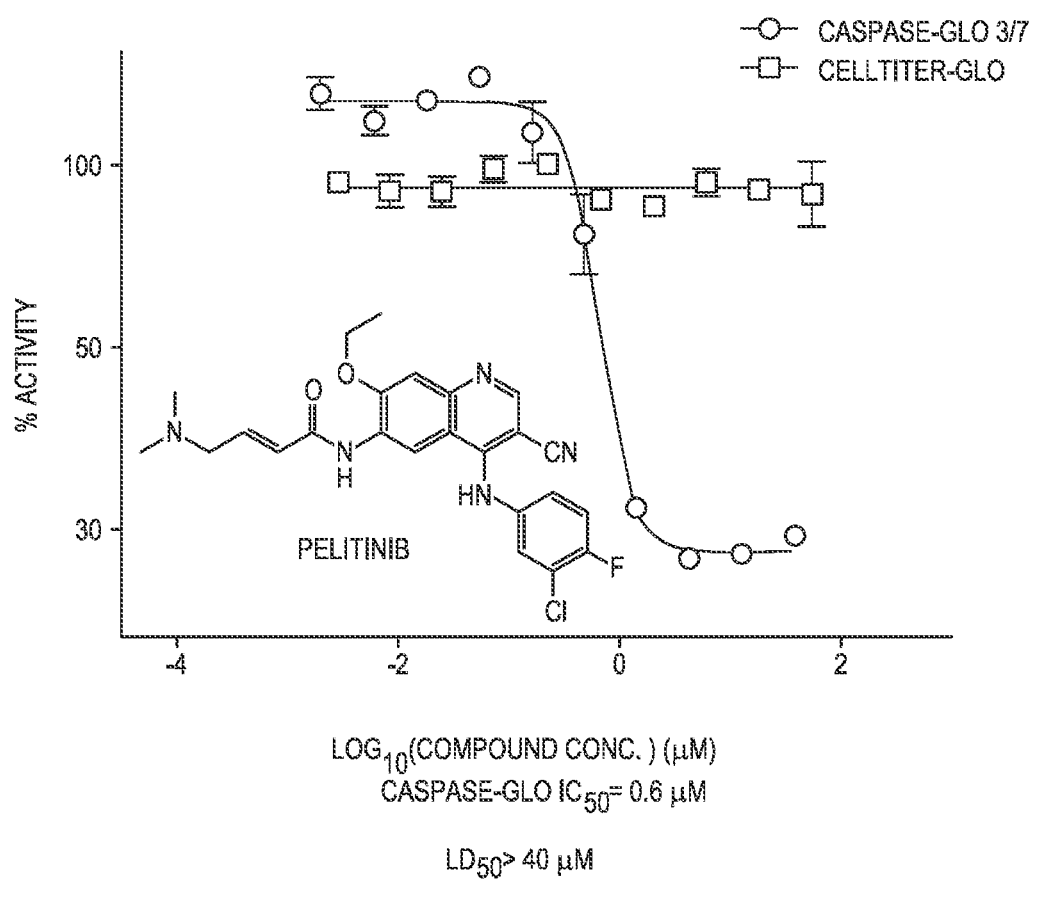
FIG. 2 shows that the EGFR inhibitor Pelitinib (whose structure is shown) protects against cisplatin-induced hair cell loss. Pelitinib is an irreversible inhibitor of EGFR that exhibits protective effects against cisplatin-induced Caspase-3/7 activity in HEI-OC1 cells with $IC_{50}$ of 0.6 µM (cisplatin-Caspase-Glo 3/7) and $LD_{50}$ of >40 µM (CELLTI-TER-GLO).

Her2 inhibitor MUBRITINIB (TAK 165) exhibited protective effects against cisplatin-induced Caspase-3/7 activity in HEI-OC1 cells with an $IC_{50}$ of 4 nM and $LD_{50}$ of >55 µM; and protected against cisplatin-induced hair cell loss in mouse cochlear explants with $IC_{50}$ of 2.5 nM and $LD_{50}$ of >500 nM (Therapeutic Index of >200) (FIG. 1). Similarly, the pan-ErbB inhibitor, PELITINIB, was found to exhibit protective effects against cisplatin-induced Caspase-3/7 activity in HEI-OC1 cell loss with $IC_{50}$ of 0.6 µM and $LD_{50}$ of 40 µM (FIG. 2). Moreover, with 1 hour pre-incubation, PELITINIB exhibited 49% protection of outer hair cells against cisplatin-induced hair cell loss in mouse cochlear explants (N=3).

Similarly, the pan-ErbB inhibitor, PELITINIB, was found to exhibit protective effects against cisplatin-induced Caspase-3/7 activity in HEI-OC1 cell loss with $IC_{50}$ of 0.6 µM and $LD_{50}$ of 40 µM (FIG. 2). Moreover, with 1 hour pre-incubation, PELITINIB exhibited 49% protection of outer hair cells against cisplatin-induced hair cell loss in mouse cochlear explants (N=3).

Figure 3:
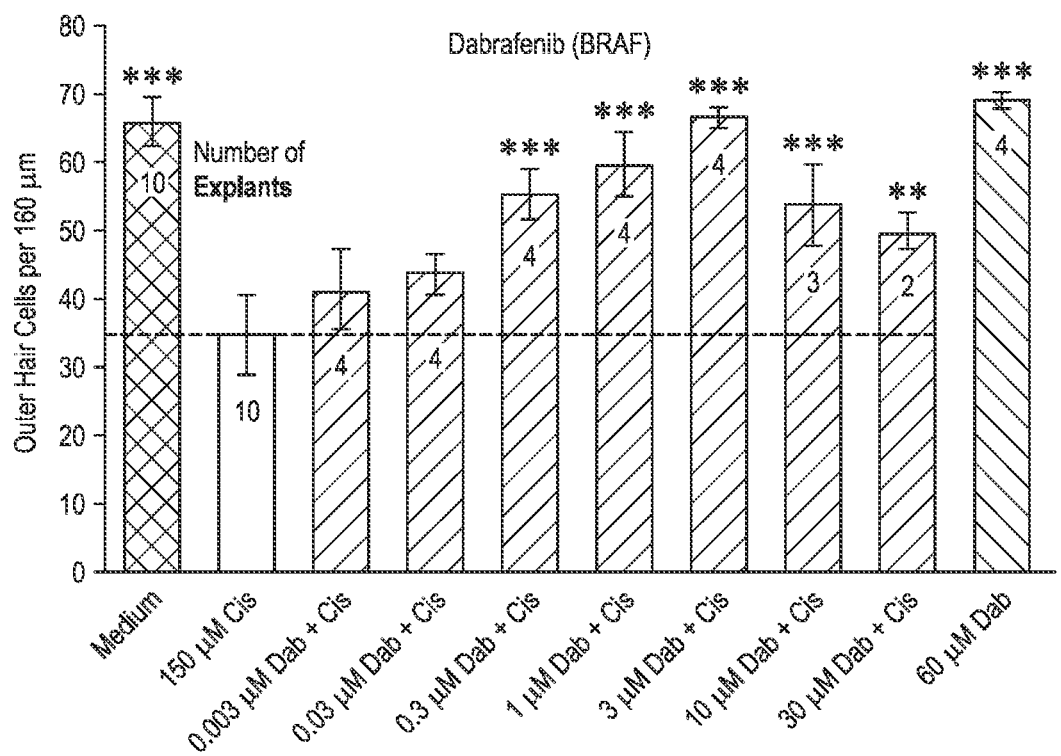
FIG. 3 shows dose-response of dabrafenib (Dab) in mouse cochlear explants treated with or without cisplatin. Dab alone or Dab added 1 h before cisplatin (150 µM) to P3 FVB cochlear explants for 24 h. Number of explants for each dose of Dab was shown. *: P<0.001; : P<0.01; *: P<0.05 (Student's T-test) comparing to Cis alone.
Figure 11A:
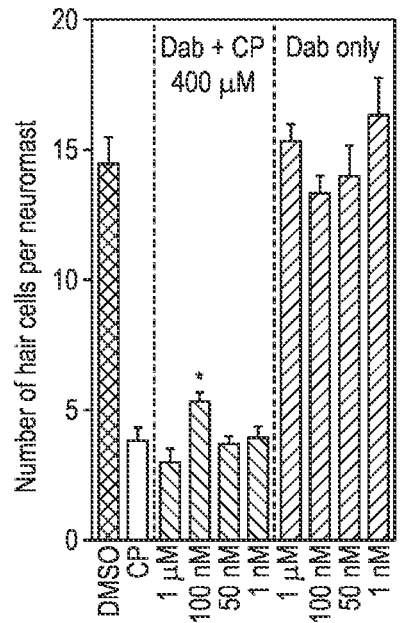
FIGS. 11A, 11B, 11C and 11D show compounds protective effect in Zebrafish (Dabrafenib, Mubritinib, Crenolanib, and SNS-314). Lateral line neuromasts of zebrafish were stained and number of hair cells per neuromast were counted. Cisplatin (CP): 400 μM. *, , and *: P<0.05, 0.01, and 0.001 compared to CP alone.

B-Raf inhibitors protected outer hair cells against cisplatin injury in mouse cochlear explants. B-Raf inhibitor Dabrafenib (BRAF) (FIG. 3A) exhibited protective cisplatin-induced hair cell loss in mouse cochlear explants with $IC_{50}$ of 0.0300 µM and $LD_{50}$ of 13.47 µM (Therapeutic Index of greater than 2000). Additionally, Dabrafenib (BRAF) showed Zebrafish compound cisplatin protection at 0.100 µM (FIG. 11A).

Additionally, the B-Raf inhibitor VEMURAFENIB (BRAF) (FIG. 4B) exhibited protective cisplatin-induced hair cell loss in mouse cochlear explants with $IC_{50}$ of ~0.2 µM and $LD_{50}$ of greater than 3 µM (Therapeutic Index of greater than 15). B-Raf inhibitor PLX-4750 (BRAF) (FIG. 4D) exhibited protective cisplatin-induced hair cell loss in mouse cochlear explants with $IC_{50}$ of 0.2 µM and $LD_{50}$ of greater than 3 µM. (Therapeutic Index of greater than 15). B-Raf inhibitor RAF-265 (BRAF) (FIG. 4E) exhibited protective cisplatin-induced hair cell loss in mouse cochlear explants with $IC_{50}$ of 0.02 µM and $LD_{50}$ of greater than 3 µM (Therapeutic Index of greater than 150).

Figure 4C:
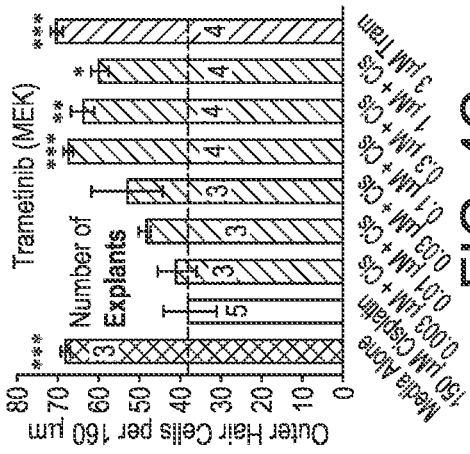
FIGS. 4B-4E show in addition to dabrafenib, three B-Raf inhibitors (Vemurafenib, PLX-4720, and RAF-265 shown) and one MEK1/2 inhibitors (Trametinib shown) protected in the cochlear explant culture assay against cisplatin-induced hair cell death. Dose-responses of the compounds in P3 FVB mouse cochlear explants treated with or without cisplatin were shown. See FIG. 3 for meaning of other labels.
Figure 4E:
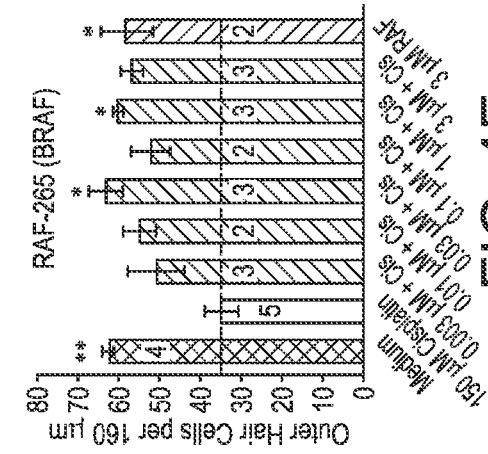
Figure 4B:
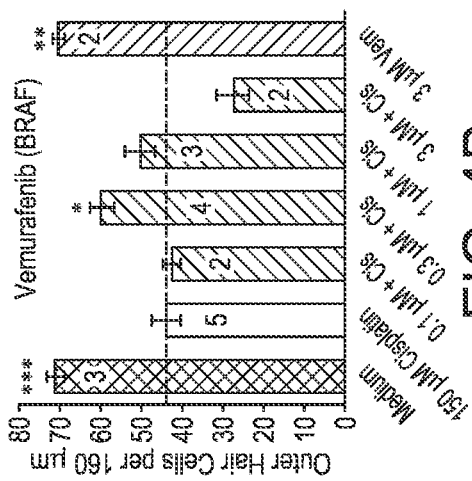
Figure 4D:
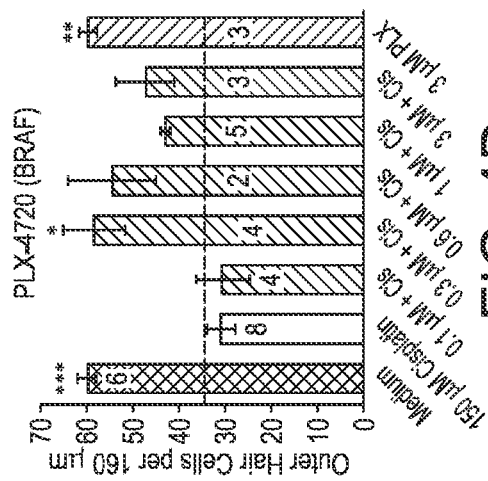

MEK inhibitors protected outer hair cells against cisplatin injury in cochlear explants as shown in FIG. 4C MEK inhibitor TRAMETINIB (MEK) exhibited protective cisplatin-induced hair cell loss in mouse cochlear explants with ICso of 0.05 µM and $LD_{50}$ of greater than 3 µM (Therapeutic Index of greater than 60).

Figure 4A:
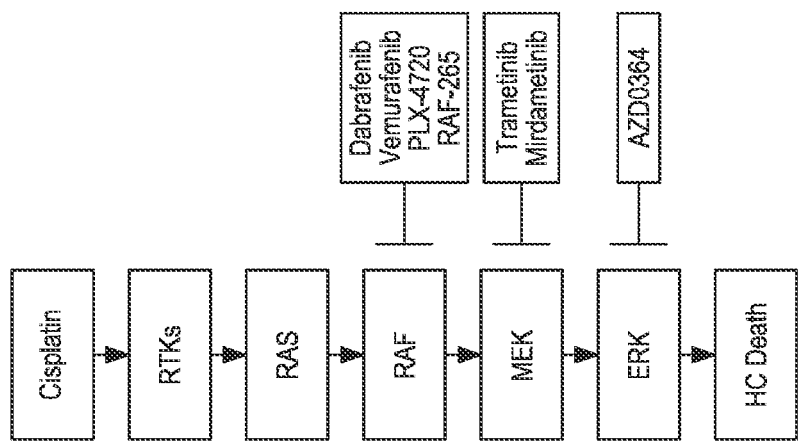
FIG. 4A shows signaling cascade of RTKs (receptor tyrosine kinases), RAS, RAF, MEK, and ERK in cisplatin-induced hair cell death and current small molecule inhibitors for RAF, MEK and ERK in otoprotection.

As illustrated in FIG. 4A inhibitor mitigate cisplatin along the signaling cascade.

Example 2 Inhibitors Mitigate Cisplatin Activated B-Raf Signaling Cascade

Figures 5A, 5B:
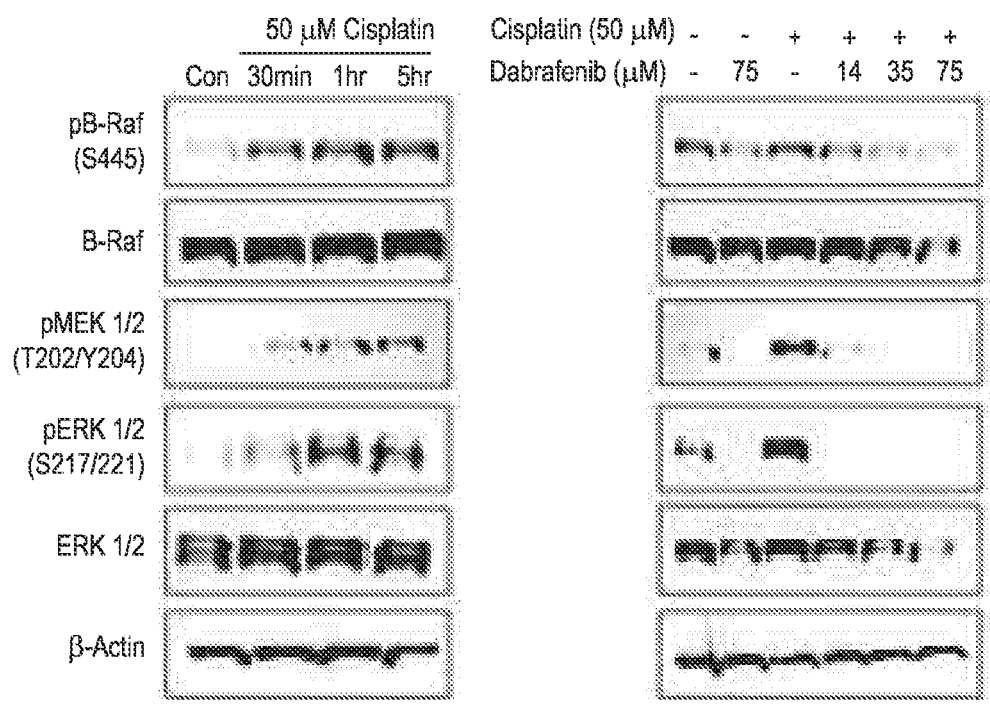
FIGS. 5A and 5B shows Dabrafenib mitigates cisplatin activated B-Raf signaling cascade in HEI-OC1 cells. Western blots show representative changes of each signaling molecule upon cisplatin and Dab treatment at specific doses (5B) and times (5A).

As shown in FIGS. 5A and 5B, B-Raf, ERK, and MEK become phosphorylated and activated in HEL-OC1 cells upon 50 µM cisplatin treatment in a time-dependent manner. DABRAFENIB treatment mitigates cisplatin-mediated μM, 1 hour activation of B-RAF, ERK and MEK in HEL-OC1 cells in a does dependent manner.

Example 3 Dabrafenib is Protective Against Cisplatin-Induced Hearing Loss in Adult Mice when Delivered Orally In Vivo FIG. 6A shows a schedule of administration of dabrafenib and cisplatin to adult FVB mice (males and females). FIG. 6B shows reduced ABR threshold shifts of 11.8-15.0 dB on average were recorded on day 21 after first day of cisplatin and dabrafenib co-treatment, mean±SEM, *, P<0.05, compared to cisplatin alone by two-way ANOVA followed by a Bonferroni comparison.

Example 4 Dabrafenib is Protective Against Noise-Induced Hearing Loss in Adult Mice when Delivered Orally In Vivo FIG. 7A shows the schedule of administration of dabrafenib and noise exposure to FVB mice (males and females). FIG. 7B shows reduced ABR threshold shifts of 18.1-21.9 dB on average were recorded on day 14 after first day of dabrafenib and noise exposure, mean±SEM, , P<0.01, *, P<0.001, compared to carrier by two-way ANOVA followed by a Bonferroni comparison.

Now referring to FIGS. 8A and 8B, Dabrafenib is protective against noise-induced hearing loss in adult mice when delivered orally forty-five minutes before the noise exposure. (A) Schedule of administration of dabrafenib and noise exposure to FVB mice (males and females). (B) Reduced ABR threshold shifts of 18.1-21.9 dB in average were recorded on day 14 after first day of dabrafenib and noise exposure, mean±SEM, , P<0.01, *, P<0.001, compared to carrier by two-way ANOVA followed by a Bonferroni comparison.

Example 5: a Combination of Inhibitors ACT Synergistically

Now referring to FIG. 9, testing of a B-Raf/MEK1/2 inhibitor combination in mouse cochlear explant cultures. Compounds alone or combination of the compounds were added 1 h before cisplatin (150 μM) to P3 FVB cochlear explants for 24 h, and number of outer hair cells per 160 μm of middle turn regions of the cochlea were counted by phalloidin staining, mean±SEM, P=*<0.05, P=***<0.001, compared to cisplatin alone by unpaired two-tailed Student's t-test. The initial molar ratio between the compounds tested was determined by the ratio given currently to cancer patients (dabrafenib at 150 mg twice daily plus trametinib at 2 mg once daily).

Example 6 Protective Effects are Shown in Zebrafish Lateral Line Neuromasts In Vivo Methods of using a zebrafish model system to evaluate small molecules capable of decreasing, inhibiting or preventing sensory hair cell damage or death are provided. Zebrafish are an advantageous animal model system for studying causes and prevention of hearing loss in comparison to mammalian animal model systems. The relative inaccessibility of hair cells in mammalian organisms limits their use as a high throughput model for identifying compounds that would prevent toxin mediated and other forms of hair cell death from occurring. The lateral line neuromast hair cells of zebrafish (Danio rerio) are structurally and functionally similar to mammalian sensory hair cells. Compounds SNS-314 (FIG. 10A) and crenolanib (FIG. 10B) protected in the cochlear explant culture assay against cisplatin-induced hair cell death. Dose-response of compounds SNS-314 and crenolanib in mouse cochlear explants treated with or without cisplatin. Compounds alone or compounds added 1 h before cisplatin (150 μM) to P3 FVB cochlear explants for 24 h, and number of outer hair cells per 160 μm of middle turn regions of the cochlea were counted by phalloidin staining, mean±SEM, P=*<0.05, P=<0.005, *P<0.0005 compared to cisplatin alone by unpaired two-tailed Student's t-test.

Figure 11B:
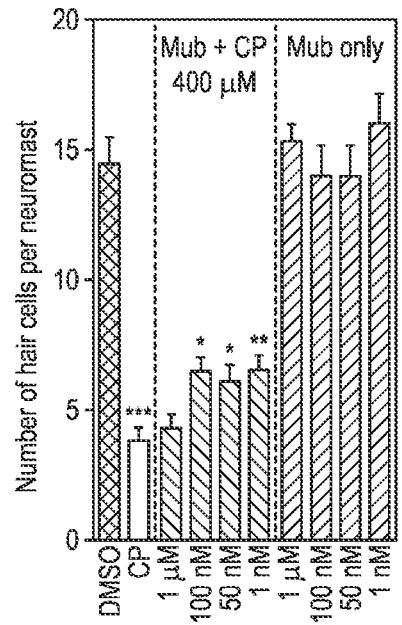
Figure 11C:
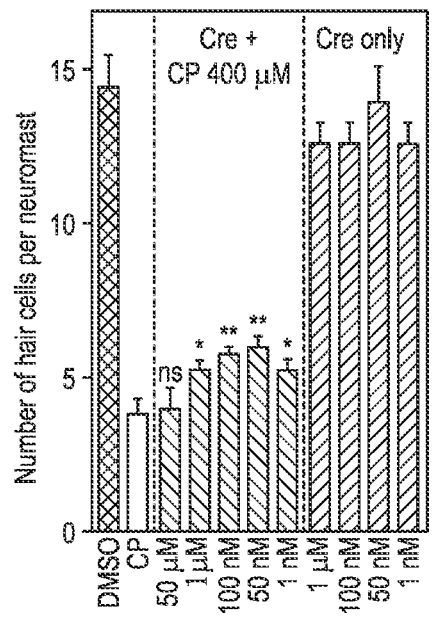
Figure 11D:
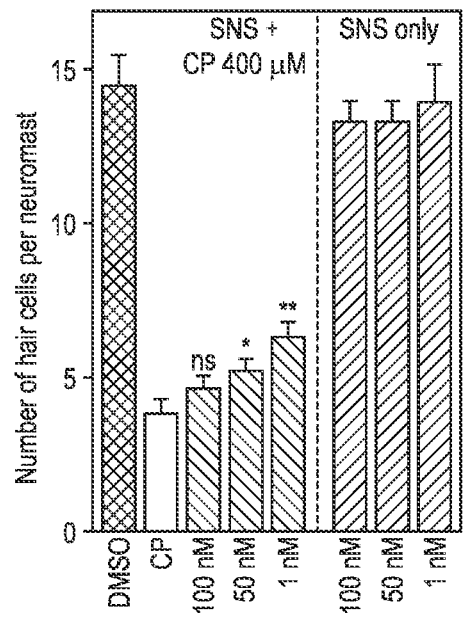

Protection of zebrafish lateral line neuromast hair cells in vivo. Five days post-fertilization Tg(brn3c: GFP) larvae were incubated with vehicle alone (DMSO), 400 μM of cisplatin (CP) for 6 hours or pre-treated with one of the compounds: dabrafenib (FIG. 11A), mubritinib (FIG. 11B), crenolanib (FIG. 11C) or SNS-314 (FIG. 11D) for 1 hour followed by a 6 hours co-incubation with the compound tested and CP 400 μM. After the treatment, animals were transferred to fresh fish water to recover for 1 hour and then fixed and immunostained for GFP and otoferlin. Quantification of the number of hair cells per neuromast after the different treatments represented as mean+/−SEM. Student's t test was performed, *p<0.05, p<0.01, *p<0.001, compared versus CP 400 μM. Neuromasts inspected: SO3 (supraorbital line neuromast) and O1-2 (otic line neuromasts) from at least 3 different animals.

Example 7 Synergistic Effect of Two Inhibitors

Figure 12:
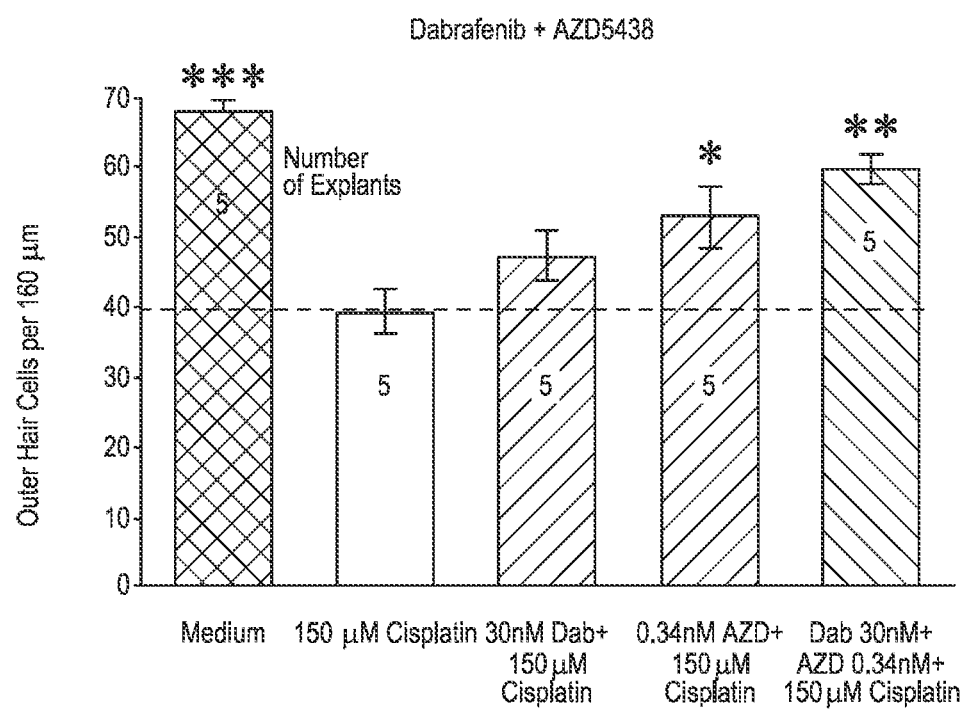
FIG. 12 shows the compounds Dabrafenib (a B-Raf kinase inhibitor, 30 nM) and AZD5438 (a CDK2 kinase inhibitor, 0.34 nM) protects against cispiatin, better than individual inhibitor, in mouse cochlear explants.

FIG. 12 shows the compounds Dabrafenib (a B-Raf kinase inhibitor) and AZD5438 (a CDK2 kinase inhibitor) protects against cisplatin and noise ototoxicity, better than individual inhibitor, in mouse cochlear explants and mice in vivo. B-Raf/CDK2 inhibitor combination protects cisplatin induced hair cell loss in mouse cochlear explants. Compounds alone (purple bar) or combination of the compounds were added 1 h before cisplatin (150 μM) to P3 FVB cochlear explants for 24 hrs, and number of outer hair cells per 160 μm of middle turn regions of the cochlea were counted by phalloidin staining, mean±SEM, P=*<0.05, P=**<0.005, compared to cisplatin alone by unpaired two-tailed Student's t-test. The initial AZD5438/dabrafenib combination tested was in the same molar ratio (0.34/30).

FIG. 13A-13D show oral delivery of the combination of inhibitors provides protection effects that are significantly better than the use of individual compound.

B-Raf/CDK2 inhibitor combination protects fully against noise induced hearing loss in mice when delivered orally. In this example, compounds for oral delivery were dissolved in the carrier 10% DMSO, 40% PF5300, 5% Tween-80 and 45% saline (0.9% NaCl) and were given in a volume of 10 ml/kg. Schedules of drugs and noise levels are shown in FIG. 13A. In FIG. 13B Dabrafenib (2×60 mg/kg/day) is given by oral delivery continuously for 3 days post-noise. In FIG. 13C AZD5438 (2×35 mg/kg/day) is given by oral delivery continuously for 3 days post-noise. In FIG. 13D complete protection against noise is achieved with combination of the two drugs for 3 days post-noise (dabrafenib (2×60 mg/kg/day) and AZD5438 (2×35 mg/kg/day), mean±SEM, *, P<0.05, **, P<0.01, compared to carrier alone by unpaired two-tailed Student's t-test

We claim:

1. A pharmaceutical composition comprising a synergistic combination of an inhibitor of epidermal growth factor receptor (EGFR) signaling comprising dabrafenib and a CDK2 inhibitor comprising AZD5438, wherein said synergistic combination protects against cisplatin induced and noise induced hearing loss in a mammal.

2. The pharmaceutical composition of claim 1 wherein the synergistic combination is formulated for oral delivery in a liquid carrier.

3. The pharmaceutical composition of claim 1 further comprised of: a sufficient amount of trametinib to prevent hearing loss due to cisplatin treatment.

4. The pharmaceutical composition of claim 3 wherein the sufficient amount of trametinib is 2 mg/kg in mice or an equivalent dosage for a human twice daily.

5. The pharmaceutical composition of claim 1, wherein the pharmaceutical composition is formulated for oral delivery.

6. The pharmaceutical composition of claim 1, wherein the pharmaceutical composition is formulated for a direct route of administration to the inner ear.

7. The pharmaceutical composition of claim 1, wherein the pharmaceutical composition is formulated for parenteral delivery.

8. A kit formulated to protect against cisplatin induced hearing loss comprising: a synergistic combination of dabrafenib in an amount sufficient to prevent cisplatin induced hearing loss, and AZD5438 in an amount sufficient to prevent cisplatin induced hearing loss and cisplatin.

9. The kit of claim 8, further comprising one or more protective or regenerative agents.

* * * * *